US012044672B2

(12) United States Patent
Shanai et al.

(10) Patent No.: US 12,044,672 B2
(45) Date of Patent: Jul. 23, 2024

(54) PHYSICAL QUANTITY ESTIMATING SYSTEM, APPROXIMATE FUNCTION GENERATING APPARATUS, PHYSICAL QUANTITY ESTIMATING APPARATUS, PROGRAM, RECORDING MEDIUM, AND PHYSICAL QUANTITY ESTIMATING METHOD

(71) Applicant: Proterial, Ltd., Tokyo (JP)

(72) Inventors: Daisuke Shanai, Tokyo (JP); Tomonori Watanabe, Tokyo (JP); Takahiro Suzuki, Tokyo (JP); Tamotsu Kibe, Tokyo (JP); Takehiko Tani, Tokyo (JP)

(73) Assignee: PROTERIAL, LTD., Tokyo (JP)

( * ) Notice: Subject to any disclaimer, the term of this patent is extended or adjusted under 35 U.S.C. 154(b) by 0 days.

(21) Appl. No.: 18/240,553

(22) Filed: Aug. 31, 2023

(65) Prior Publication Data

US 2024/0077466 A1 Mar. 7, 2024

(30) Foreign Application Priority Data

Sep. 2, 2022 (JP) .................. 2022-140016

(51) Int. Cl.
*G01N 33/44* (2006.01)
(52) U.S. Cl.
CPC .................. *G01N 33/442* (2013.01)
(58) Field of Classification Search
CPC ...................... G01N 33/442; G01N 2033/0003

USPC ............. 73/865.8, 866, 24.05, 32 R; 374/16; 702/127, 137
See application file for complete search history.

(56) References Cited

U.S. PATENT DOCUMENTS

2017/0371980 A1 12/2017 Mallapragada et al.
2022/0308039 A1* 9/2022 Kawamura .......... G01N 33/442

FOREIGN PATENT DOCUMENTS

| CN | 113205859 A | * | 8/2021 | ............. G16C 20/30 |
| JP | 2018-156689 A | | 10/2018 | |
| JP | 2022087429 A | | 6/2022 | |
| JP | 2022108269 A | | 7/2022 | |
| WO | 2022080443 A1 | | 4/2022 | |

OTHER PUBLICATIONS

Japanese Decision to Grant a Patent dated Jan. 31, 2023, in connection with corresponding JP Application No. 2022-140016 (5 pp., including machine-generated English translation).

* cited by examiner

*Primary Examiner* — Robert R Raevis
(74) *Attorney, Agent, or Firm* — McCormick, Paulding & Huber PLLC

(57) ABSTRACT

A first synthesized characteristic value calculated based on a first blending ratio of constituent materials contained in a first composite material and on a first characteristic value corresponding to the constituent materials contained in the first composite material, as well as first blending information of the constituent materials contained in the first composite material are used as input parameters (explanatory variables) for an approximate function to estimate a value of physical quantity (objective variable) for the first composite material.

14 Claims, 19 Drawing Sheets

FIG. 10

| BLENDING NUMBER | RESIN | | | | | | | FLAME RETARDANT | | | ANTIOXIDANT | | LUBRICANT | | | COLORING AGENT | CROSS-LINKING AID | TENSILE STRENGTH (PHYSICAL QUANTITY) |
|---|---|---|---|---|---|---|---|---|---|---|---|---|---|---|---|---|---|---|
| | A | B | C | D | E | F | G | H | I | J | K | L | M | N | O | P | Q | |
| ID1 | | 20 | 50 | | 30 | | | 200 | | | 1 | 2 | 1 | 2 | | 2 | 4 | 8.3347 |
| ID2 | | 20 | 50 | | 30 | | | 200 | | | 1 | 2 | 1 | 2 | | 2 | 4 | 13.854 |
| ID3 | | | 70 | | 30 | | | 200 | | | 1 | 2 | 1 | 2 | | 2 | 4 | 6.6383 |
| ID4 | | | 70 | | 30 | | | 200 | | | 1 | 2 | 1 | 2 | | 2 | 4 | 11.098 |
| ID5 | 45 | | | 40 | | 15 | | | 180 | | 1 | 2 | 1 | | 2 | 2 | 4 | 5.8226 |
| ID6 | 45 | | | 40 | | 15 | | | 180 | | 1 | 2 | 1 | | 2 | 2 | 4 | 14.425 |
| ID7 | 45 | | | 40 | | 15 | | | 200 | | 1 | 2 | 1 | | 2 | 2 | 4 | 5.8352 |
| ID8 | 45 | | | 40 | | 15 | | | 200 | | 1 | 2 | 1 | | 2 | 2 | 4 | 15.485 |
| ID9 | 45 | | | 40 | 15 | | | | 200 | | 1 | 2 | 1 | | 2 | 2 | 4 | 5.0462 |
| ID10 | 45 | | | 40 | 15 | | | | 200 | | 1 | 2 | 1 | | 2 | 2 | 4 | 13.562 |
| ID11 | 45 | | | 45 | | 10 | | | 200 | | 1 | 2 | 1 | | 2 | 2 | 4 | 4.9838 |
| ID12 | 45 | | | 45 | | 10 | | | 200 | | 1 | 2 | 1 | | 2 | 2 | 4 | 12.348 |
| ID13 | 40 | | | 45 | | 15 | | | 200 | | 1 | 2 | 1 | | 2 | 2 | 4 | 5.4539 |
| ID14 | 40 | | | 45 | | 15 | | | 200 | | 1 | 2 | 1 | | 2 | 2 | 4 | 13.93 |
| ID15 | 45 | | | 40 | | 15 | | | 100 | 100 | 1 | 2 | 1 | | 2 | 2 | 4 | 5.1082 |
| ID16 | 45 | | | 40 | | 15 | | | 100 | 100 | 1 | 2 | 1 | | 2 | 2 | 4 | 9.2177 |
| ID17 | 45 | | | 40 | | 15 | | | | 200 | 1 | 2 | 1 | | 2 | 2 | 4 | 4.4019 |
| ID18 | 40 | | | 40 | | 15 | | | 200 | 200 | 1 | 2 | 1 | | 2 | 2 | 4 | 7.3505 |
| ID19 | 45 | | | 40 | | | 15 | | | 200 | 1 | 2 | 1 | | 2 | 2 | 4 | 5.0503 |
| ID20 | 45 | | | 40 | | | 15 | | | 200 | 1 | 2 | 1 | | 2 | 2 | 4 | 7.3003 |

FIG. 11

| BLENDING NUMBER | SYNTHESIZED CHARACTERISTIC VALUE | | | | | CATEGORICAL VARIABLE | | | | IRRADIATION DOSE | TENSILE STRENGTH (PHYSICAL QUANTITY) |
|---|---|---|---|---|---|---|---|---|---|---|---|
| | FILLER VOLUME RATIO | AMOUNT OF MALEIC ANHYDRIDE DENATURATION | AMOUNT OF CRYSTALS | AMOUNT OF VINYL ACETATE GROUP | FILLER SURFACE AREA | CAT1 | CAT2 | CAT3 | CAT4 | | |
| ID1 | 0.792 | 0.3 | 4.919 | 26.9 | 1261 | 1 | 0 | 1 | 0 | 0 | 8.3347 |
| ID2 | 0.792 | 0.3 | 4.919 | 26.9 | 1261 | 1 | 0 | 1 | 0 | 75 | 13.854 |
| ID3 | 0.795 | 0.3 | 0 | 29.5 | 1261 | 1 | 0 | 1 | 0 | 0 | 6.6383 |
| ID4 | 0.795 | 0.3 | 0 | 29.5 | 1261 | 1 | 0 | 1 | 0 | 75 | 11.098 |
| ID5 | 0.718 | 0.3 | 26.83 | 32.45 | 723.2 | 1 | 0 | 0 | 1 | 0 | 5.8226 |
| ID6 | 0.718 | 0.3 | 26.83 | 32.45 | 723.2 | 1 | 0 | 0 | 1 | 90 | 14.425 |
| ID7 | 0.797 | 0.3 | 26.83 | 32.45 | 803.6 | 1 | 0 | 0 | 1 | 0 | 5.8352 |
| ID8 | 0.797 | 0.3 | 26.83 | 32.45 | 803.6 | 1 | 0 | 0 | 1 | 90 | 15.485 |
| ID9 | 0.797 | 0.15 | 26.83 | 32.45 | 803.6 | 1 | 0 | 0 | 1 | 0 | 5.0462 |
| ID10 | 0.797 | 0.15 | 26.83 | 32.45 | 803.6 | 1 | 0 | 0 | 1 | 90 | 13.562 |
| ID11 | 0.805 | 0.2 | 26.83 | 32.45 | 803.6 | 1 | 0 | 0 | 1 | 0 | 4.9838 |
| ID12 | 0.805 | 0.2 | 26.83 | 32.45 | 803.6 | 1 | 0 | 0 | 1 | 90 | 12.348 |
| ID13 | 0.801 | 0.3 | 23.85 | 34.6 | 803.6 | 1 | 0 | 0 | 1 | 0 | 5.4539 |
| ID14 | 0.801 | 0.3 | 23.85 | 34.6 | 803.6 | 1 | 0 | 0 | 1 | 90 | 13.93 |
| ID15 | 0.797 | 0.3 | 26.83 | 32.45 | 663.5 | 1 | 1 | 0 | 1 | 0 | 5.1082 |
| ID16 | 0.797 | 0.3 | 26.83 | 32.45 | 663.5 | 1 | 1 | 0 | 1 | 90 | 9.2177 |
| ID17 | 0.797 | 0.3 | 26.83 | 32.45 | 523.4 | 0 | 1 | 0 | 1 | 0 | 4.4019 |
| ID18 | 0.797 | 0.3 | 26.83 | 32.45 | 523.4 | 0 | 1 | 0 | 1 | 90 | 7.3505 |
| ID19 | 0.797 | 0.6 | 26.83 | 32.45 | 523.4 | 0 | 1 | 0 | 1 | 0 | 5.0503 |
| ID20 | 0.797 | 0.6 | 26.83 | 32.45 | 523.4 | 0 | 1 | 0 | 1 | 90 | 7.3003 |

FIG. 12

| BLENDING NUMBER | RESIN | | | | FLAME RETARDANT | ANTIOXIDANT | | LUBRICANT | | COLORING AGENT | CROSS-LINKING AID |
|---|---|---|---|---|---|---|---|---|---|---|---|
| | A | D | F | G | I | K | L | M | O | P | Q |
| ID100 | 45 | 40 | 15 | | 160 | 1 | 2 | 1 | 2 | 2 | 4 |
| ID101 | 45 | 40 | 15 | | 160 | 1 | 2 | 1 | 2 | 2 | 4 |
| ID102 | 45 | 40 | 15 | | 160 | 1 | 2 | 1 | 2 | 2 | 4 |
| ID103 | 45 | 40 | 15 | | 160 | 1 | 2 | 1 | 2 | 2 | 4 |
| ID104 | 35 | 50 | 15 | | 160 | 1 | 2 | 1 | 2 | 2 | 4 |
| ID105 | 35 | 50 | 15 | | 160 | 1 | 2 | 1 | 2 | 2 | 4 |
| ID106 | 35 | 50 | 15 | | 160 | 1 | 2 | 1 | 2 | 2 | 4 |
| ID107 | 35 | 50 | 15 | | 160 | 1 | 2 | 1 | 2 | 2 | 4 |
| ID108 | 25 | 60 | 15 | | 160 | 1 | 2 | 1 | 2 | 2 | 4 |
| ID109 | 25 | 60 | 15 | | 160 | 1 | 2 | 1 | 2 | 2 | 4 |
| ID110 | 25 | 60 | 15 | | 160 | 1 | 2 | 1 | 2 | 2 | 4 |
| ID111 | 25 | 60 | 15 | | 160 | 1 | 2 | 1 | 2 | 2 | 4 |
| ID112 | 45 | 48 | 7 | | 160 | 1 | 2 | 1 | 2 | 2 | 4 |
| ID113 | 45 | 48 | 7 | | 160 | 1 | 2 | 1 | 2 | 2 | 4 |
| ID114 | 45 | 48 | 7 | | 160 | 1 | 2 | 1 | 2 | 2 | 4 |
| ID115 | 45 | 48 | 7 | | 160 | 1 | 2 | 1 | 2 | 2 | 4 |
| ID116 | 45 | 48 | | 7 | 160 | 1 | 2 | 1 | 2 | 2 | 4 |
| ID117 | 45 | 48 | | 7 | 160 | 1 | 2 | 1 | 2 | 2 | 4 |
| ID118 | 45 | 48 | | 7 | 160 | 1 | 2 | 1 | 2 | 2 | 4 |
| ID119 | 45 | 48 | | 7 | 160 | 1 | 2 | 1 | 2 | 2 | 4 |

FIG. 13

| BLENDING NUMBER | FIRST SYNTHESIZED CHARACTERISTIC VALUE ||||||| FIRST CATEGORICAL VARIABLE |||| FIRST IRRADIATION DOSE |
|---|---|---|---|---|---|---|---|---|---|---|---|
| | FILLER VOLUME RATIO | AMOUNT OF MALEIC ANHYDRIDE DENATURATION | AMOUNT OF CRYSTALS | AMOUNT OF VINYL ACETATE GROUP | FILLER SURFACE AREA | CAT1 | CAT2 | CAT3 | CAT4 | |
| ID100 | 0.6 | 0.3 | 27 | 32 | 643 | 1 | 0 | 0 | 1 | 0 |
| ID101 | 0.6 | 0.3 | 27 | 32 | 643 | 1 | 0 | 0 | 1 | 75 |
| ID102 | 0.6 | 0.3 | 27 | 32 | 643 | 1 | 0 | 0 | 1 | 100 |
| ID103 | 0.6 | 0.3 | 27 | 32 | 643 | 1 | 0 | 0 | 1 | 120 |
| ID104 | 0.6 | 0.3 | 21 | 36 | 643 | 1 | 0 | 0 | 1 | 0 |
| ID105 | 0.6 | 0.3 | 21 | 36 | 643 | 1 | 0 | 0 | 1 | 75 |
| ID106 | 0.6 | 0.3 | 21 | 36 | 643 | 1 | 0 | 0 | 1 | 100 |
| ID107 | 0.6 | 0.3 | 21 | 36 | 643 | 1 | 0 | 0 | 1 | 120 |
| ID108 | 0.7 | 0.3 | 15 | 40 | 643 | 1 | 0 | 0 | 1 | 0 |
| ID109 | 0.7 | 0.3 | 15 | 40 | 643 | 1 | 0 | 0 | 1 | 75 |
| ID110 | 0.7 | 0.3 | 15 | 40 | 643 | 1 | 0 | 0 | 1 | 100 |
| ID111 | 0.7 | 0.3 | 15 | 40 | 643 | 1 | 0 | 0 | 1 | 120 |
| ID112 | 0.6 | 0.2 | 27 | 36 | 643 | 1 | 0 | 0 | 1 | 0 |
| ID113 | 0.6 | 0.2 | 27 | 36 | 643 | 1 | 0 | 0 | 1 | 75 |
| ID114 | 0.6 | 0.2 | 27 | 36 | 643 | 1 | 0 | 0 | 1 | 100 |
| ID115 | 0.6 | 0.2 | 27 | 36 | 643 | 1 | 0 | 0 | 1 | 120 |
| ID116 | 0.6 | 0.3 | 27 | 36 | 643 | 1 | 0 | 0 | 1 | 0 |
| ID117 | 0.6 | 0.3 | 27 | 36 | 643 | 1 | 0 | 0 | 1 | 75 |
| ID118 | 0.6 | 0.3 | 27 | 36 | 643 | 1 | 0 | 0 | 1 | 100 |
| ID119 | 0.6 | 0.3 | 27 | 36 | 643 | 1 | 0 | 0 | 1 | 120 |

FIG. 14

| BLENDING NUMBER | TENSILE STRENGTH (ESTIMATED VALUE) |
|---|---|
| ID100 | 13.15 |
| ID101 | 14.1 |
| ID102 | 14.39 |
| ID103 | 12.44 |
| ID104 | 13.43 |
| ID105 | 13.78 |
| ID106 | 11.83 |
| ID107 | 12.85 |
| ID108 | 13.23 |
| ID109 | 11.15 |
| ID110 | 12.08 |
| ID111 | 12.42 |
| ID112 | 13.25 |
| ID113 | 14.26 |
| ID114 | 14.57 |
| ID115 | 12.9 |
| ID116 | 13.8 |
| ID117 | 14.06 |
| ID118 | 12.68 |
| ID119 | 13.49 |

PHYSICAL QUANTITY ESTIMATING SYSTEM, APPROXIMATE FUNCTION GENERATING APPARATUS, PHYSICAL QUANTITY ESTIMATING APPARATUS, PROGRAM, RECORDING MEDIUM, AND PHYSICAL QUANTITY ESTIMATING METHOD

CROSS-REFERENCE TO RELATED APPLICATION

This application claims foreign priority benefits under 35 U.S.C. § 119 from Japanese Patent Application No. 2022-140016, filed Sep. 2, 2022, the content of which is hereby incorporated by reference in its entirety.

TECHNICAL FIELD

The present invention relates to a physical quantity estimating system, an approximate function generating apparatus, a physical quantity estimating apparatus, a program, a recording medium, and a physical quantity estimating technique, and relates to, for example, a technique effective when applied to a technique for estimating a value of physical quantity according to a blending ratio of a resin composite material.

BACKGROUND

Japanese Patent Application Laid-Open Publication No. 2018-156689 (Patent Document 1) discloses a technique for estimating physical characteristics of a composite material by utilizing artificial intelligence.

SUMMARY

In recent years, a composite material has been developed by compounding several types of resins or blending agents to add new performance to characteristics of the resin itself. In this regard, development of a new composite material requires the material to be developed while adjusting a composition ratio of each composition until the composite material obtains a desired characteristic. This makes development of the composite material very costly. Therefore, from the viewpoint of improving efficiency of composite material development, it is desirable that a physical quantity of the composite material to be tested at an experimental planning stage can be estimated to some extent. However, for example, there are many types of blending agents in composite materials for electric wire coating materials, and a value of physical quantity would significantly vary depending on the blending composition ratio. This makes it difficult to estimate the value of physical quantity for the composite material. In light of the above, a technique in which a value of physical quantity for a composite material can be estimated with high accuracy is desired.

A physical quantity estimating system according to one embodiment is configured to estimate a value of physical quantity for a composite material containing two or more materials belonging to a plurality of different materials as constituent materials. The physical quantity estimating system comprises: an approximate function generating unit configured to generate, when a first synthesized characteristic value of a first composite material whose value of physical quantity is unknown and first blending information including material names and a first blending ratio of the constituent materials contained in the first composite material are input, an approximate function for outputting the value of physical quantity for the first composite material; a synthesized characteristic value calculating unit configured to calculate the first synthesized characteristic value of the first composite material based on the first blending ratio of the constituent materials contained in the first composite material and on a first characteristic value corresponding to the constituent materials contained in the first composite material; and a physical quantity estimating unit configured to estimate the value of physical quantity for the first composite material based on the first synthesized characteristic value, the first blending information, and the approximate function.

An approximate function generating apparatus according to one embodiment is a component of a physical quantity estimating system configured to estimate a value of physical quantity for a composite material containing two or more materials belonging to a plurality of different materials as constituent materials. The approximate function generating apparatus comprises an approximate function generating unit configured to generate, when a first synthesized characteristic value of a first composite material whose value of physical quantity is unknown and first blending information including material names and a first blending ratio of the constituent materials contained in the first composite material are input, an approximate function for outputting the value of physical quantity for the first composite material. Here, the first synthesized characteristic value is a value calculated based on the first blending ratio of the constituent materials contained in the first composite material and on a first characteristic value corresponding to the constituent materials contained in the first composite material.

A program according to one embodiment is configured to cause a computer to execute a process of estimating a value of physical quantity for a composite material containing two or more materials belonging to a plurality of different materials as constituent materials. The program includes an approximate function generating process configured to generate, when a first synthesized characteristic value of a first composite material whose value of physical quantity is unknown and first blending information including material names and a first blending ratio of the constituent materials contained in the first composite material are input, an approximate function for outputting the value of physical quantity for the first composite material. Here, the first synthesized characteristic value is a value calculated based on the first blending ratio of the constituent materials contained in the first composite material and on a first characteristic value corresponding to the constituent materials contained in the first composite material.

A physical quantity estimating apparatus according to one embodiment is a component of a physical quantity estimating system configured to estimate a value of physical quantity for a composite material containing two or more materials belonging to a plurality of different materials as constituent materials. The physical quantity estimating apparatus comprises: a synthesized characteristic value calculating unit configured to calculate, based on a first blending ratio of the constituent materials contained in a first composite material whose value of physical quantity is unknown and on a first characteristic value corresponding to the constituent materials contained in the first composite material, a first synthesized characteristic value of the first composite material; and a physical quantity estimating unit configured to estimate the value of physical quantity for the first composite material based on the first synthesized characteristic value, first blending information including material names and the first blending ratio of the constituent materials contained in the first composite material, and an approximate function. Here, the approximate function is a function for outputting the value of physical quantity for the first composite material when the first synthesized characteristic value and the first blending information are input.

A program according to one embodiment is configured to cause a computer to execute a process of estimating a value of physical quantity for a composite material containing two or more materials belonging to a plurality of different materials as constituent materials. The program includes: a synthesized characteristic value calculating process configured to calculate, based on a first blending ratio of the constituent materials contained in a first composite material whose value of physical quantity is unknown and on a first characteristic value corresponding to the constituent materials contained in the first composite material, a first synthesized characteristic value of the first composite material; and a physical quantity estimating process configured to estimate the value of physical quantity for the first composite material based on the first synthesized characteristic value, first blending information including material names and the first blending ratio of the constituent materials contained in the first composite material, and an approximate function. Here, the approximate function is a function for outputting the value of physical quantity for the first composite material when the first synthesized characteristic value and the first blending information are input.

A physical quantity estimating method according to one embodiment in which a computer estimates a value of physical quantity for a composite material containing two or more materials belonging to a plurality of different materials as constituent materials. The physical quantity estimating method includes: an approximate function generating step in which an approximate function generating unit of the computer generates, when a first synthesized characteristic value of a first composite material whose value of physical quantity is unknown and first blending information including material names and a first blending ratio of the constituent materials contained in the first composite material are input, an approximate function for outputting the value of physical quantity for the first composite material; a synthesized characteristic value calculating step in which a synthesized characteristic value calculating unit of the computer calculates the first synthesized characteristic value of the first composite material based on the first blending ratio of the constituent materials contained in the first composite material and on a first characteristic value corresponding to the constituent materials contained in the first composite material; and a physical quantity estimating step in which a physical quantity estimating unit of the computer estimates the value of physical quantity for the first composite material based on the first synthesized characteristic value, the first blending information, and the approximate function.

According to the embodiment, a value of physical quantity for a composite material can be estimated with high accuracy.

BRIEF DESCRIPTION OF THE DRAWINGS

FIG. 10 is a table showing data according to a specific example in which blending data and physical quantity data are combined;

FIG. 11 is a table showing synthesis-related data according to the specific example;

FIG. 12 is a table showing first blending data of a first composite material which becomes the evaluation target whose correspondence to the value of physical quantity is unknown;

FIG. 13 is a table showing data including a first synthesized characteristic value according to the specific example;

FIG. 14 is a table showing results of estimating the value of physical quantity according to the specific example;

DETAILED DESCRIPTION

Figure 1:
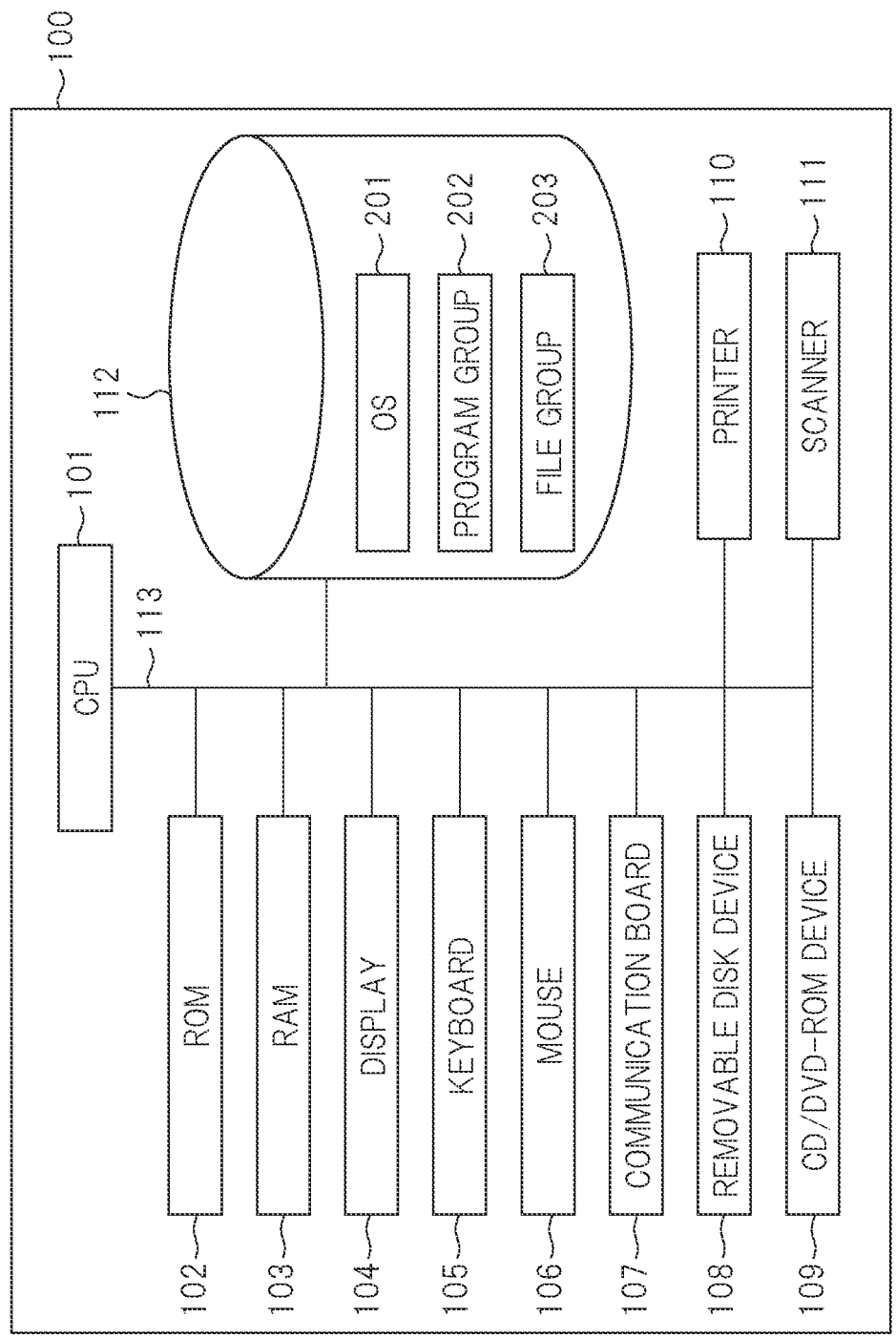
FIG. 1 is a drawing showing an example of a hardware configuration of a physical quantity estimating apparatus.

In all of the drawings used to describe the embodiments, the same members are denoted by the same reference signs, and redundant descriptions thereof are omitted as appropriate. Note that hatched lines may be added to the drawing even in plan view to clarify the drawing.

(Basic Concept)

A technical concept according to the present embodiment is one related to a physical quantity estimating system configured to estimate a value of physical quantity corresponding to a blending ratio in a composite material in which several types of resins and blending agents are compounded.

Here, an example of the composite material includes a wire coating material containing resin or blending agents, and an example of physical quantity includes elongation or tensile strength of the composite material.

Examples of resin include a polyolefin such as high-density polyethylene, low-density polyethylene or an ethylene-acrylic acid copolymer, or an elastomer such as chlorinated polyethylene. On the other hand, examples of blending agents include fillers such as talc, calcium carbonate and silica, plasticizers, cross-linking agents, and stabilizers. However, the types or the number of compositions of the resins, the blending agents or the like constituting the composite material are not limited.

Note that the technical concept according to the present embodiment is applicable not only to a composite material in which several types of resins and blending agents are compounded, but also to a composite material in which several types of magnetic materials are compounded, and an example of the physical quantity can include a magnetic susceptibility or a strength of a magnetic field (magnetic flux density).

<Description of Related Technique>

First, a related technique related to the physical quantity estimating system configured to estimate the value of physical quantity corresponding to the blending ratio will be described. The "related technique" in the present specification is not a known technique but is a technique that has problems found by the present inventors and is a premise of the present invention.

For example, as the physical quantity estimating system, it is possible to consider a related technique in which, when material names of the constituent materials constituting the composite material and a blending ratio of the constituent materials are input, a value of physical quantity of the composite material is estimated based on an approximate function for outputting the value of physical quantity of the composite material. In this related technique, for example, data in which the material names of the constituent materials, the blending ratio of the constituent materials, and the value of physical quantity corresponding to this blending ratio are known is used for teacher data, and the approximate function in which input are the material names and the blending ratio and an output is the value of physical quantity is generated.

However, in the related technique, an estimate target of the value of physical quantity is limited to the constituent materials included in the teacher data used to generate the approximate function. Namely, in a case where any constituent material that has not been used to generate the approximate function is contained in the composite material which becomes an evaluation target, estimation accuracy of the value of physical quantity of this composite material is reduced. This is because, in the related technique, since the material names of the constituent materials are used as input parameters for the approximate function, the input parameters cannot be synthesized. This will be described below for clarity.

For example, it is assumed that data whose value of physical quantity "100" is associated with a material name "high-density polyethylene", and data whose value of physical quantity "200" is associated with a material name "low-density polyethylene" are used for the teacher data to generate an approximate function of the related technique.

In this case, it is considered that, for example, the approximate function generated by the related technique is used to estimate a value of physical quantity for a composite material in which "high-density polyethylene" and "low-density polyethylene" are contained in the composite material as constituent materials and a blending ratio of the constituent materials is 50:50.

First, in the related technique, when it is considered that the input parameters for the constituent materials constituting the composite material are synthesized in order to obtain the input parameters for the composite material, an operation of "high-density polyethylene"×0.5+"low-density polyethylene"×0.5 which is an operation of "material name"×"numerical value" is obtained. Thus, an operation of synthesizing the input parameters itself would not make sense.

However, the data in which the value of physical quantity "100" is associated with the material name "high-density polyethylene" and the data in which the value of physical quantity "200" is associated with the material name "low-density polyethylene" are used for the teacher data. For this reason, in this case, it is assumed that it is possible to estimate that the value of physical quantity for the composite material is "100"×0.5+"200"×0.5="150" in the approximate function generated by the related technique without performing the operation of synthesizing the input parameters. In other words, in the related technique, it is considered that the value of physical quantity for the composite material containing "high-density polyethylene" and "low-density polyethylene" used for the teacher data can be estimated with high accuracy.

On the other hand, for example, it is considered that an approximate function generated by the related technique is used to estimate a value of physical quantity for a composite material containing "polyolefin" and "high-density polyethylene" as constituent materials of the composite material and in which a blending ratio of the constituent materials is 70:30.

In this case, first, when it is considered that the input parameters for the constituent materials constituting the composite material are synthesized in order to obtain the input parameters for the composite material, an operation of "polyolefin"×0.7+"high-density polyethylene"×0.3 which is an operation of "material name"×"numerical value" is obtained. Thus, the operation of synthesizing the input parameters itself would not make sense.

Further, in this case, "polyolefin" not included in the teacher data is contained as a constituent material of the composite material. As a result, in the approximate function generated by the related technique, since it is difficult to grasp the value of physical quantity for "polyolefin", the value of physical quantity for the composite material becomes "???"×0.7+"100"×0.3, and it would be difficult to estimate the value of physical quantity for the composite material containing "polyolefin" and "high-density polyethylene" with high accuracy.

This means that, in the approximate function using the material names as the input parameters, a synthesizing operation between the input parameters would not make sense. Thus, estimation accuracy of the value of physical quantity for the composite material containing the constituent material not used for the teacher data is reduced.

From the above, there is room for improvement in the related technique from the viewpoint of estimating, with high accuracy, the value of physical quantity for the composite material containing the constituent material not used to generate the approximate function.

Therefore, in the present embodiment, improvements have been made with respect to the room for improvement in the related technique. Hereinafter, the technical concept according to the present embodiment to which such improvements are applied will be described.

<Basic Concept According to Embodiment>

First, the present inventors noticed that the essence of the problem lies in the fact that the related technique uses the input parameter of material names which are difficult to synthesize, and as result, estimation accuracy of the value of physical quantity for the composite material containing the constituent material not used for the teacher data is reduced. The present inventors thus came to the conclusion that, for example, using input parameters related to the constituent materials that are easy to synthesize makes it possible to improve estimation accuracy of the value of physical quantity for the composite material containing the constituent material not used for the teacher data.

In this regard, the basic concept is one in which the synthesizing operation can be performed if parameters that can be expressed by numerical values are used as the input parameters related to the constituent materials, and thus, estimation accuracy of the value of physical quantity for the composite material containing the constituent material not used for the teacher data can be improved. This will be described in detail below.

For example, assume that data whose value of physical quantity "100" is associated with an input parameter "50" and data whose value of physical quantity "150" is associated with an input parameter "100" are used for the teacher data to generate an approximate function.

In this regard, first, it is considered that, for example, the value of physical quantity for the composite material that contains, as the constituent materials of the composite material, a constituent material with an input parameter "50" and a constituent material with an input parameter "100", and having the blending ratio of the constituent materials of 50:50 is estimated using the above-described approximate function. In this case, when it is considered that the input parameters for the constituent materials constituting the composite material are synthesized in order to obtain the input parameter for the composite material, an operation of "50"×0.5+"100"×0.5="75" which is an operation of "numerical value"×"numerical value" is obtained. Thus, the operation of synthesizing the input parameters can be easily performed. This makes it possible to obtain the input parameter "75" for the composite material, and inputting this input parameter "75" to the approximate function according to the basic concept makes it possible to estimate the value of physical quantity for the composite material. Therefore, according to the basic concept, the value of physical quantity for the composite material containing the constituent material used for the teacher data can be estimated with high accuracy.

Next, for example, it is considered that the value of physical quantity for the composite material that contains, as the constituent materials of the composite material, a constituent material with an input parameter "50" and a constituent material with an input parameter "75", and having the blending ratio of the constituent materials of 50:50 is estimated using the above-described approximate function.

In this case, the constituent material with the input parameter "75" not included in the teacher data is included as the constituent material of the composite material. However, in the basic concept, parameters expressed by numerical values are used as the input parameters. For this reason, in the basic concept, the input parameters for the constituent materials constituting the composite material can be synthesized in order to obtain the input parameter for the composite material. Specifically, when it is considered that the input parameters for the constituent materials constituting the composite material are synthesized, an operation of "50"×0.5+"75"×0.5="62.5" which is an operation of "numerical value"×"numerical value" is obtained. Thus, the operation of synthesizing the input parameters can be easily performed. This makes it possible to obtain the input parameter "62.5" for the composite material, and inputting this input parameter "62.5" to the approximate function according to the basic concept makes it possible to estimate the value of physical quantity for the composite material. Therefore, according to the basic concept, the value of physical quantity for the composite material containing a new constituent material not used for the teacher data can also be estimated with high accuracy. This is a result of the fact that the basic concept uses the input parameters related to the constituent materials which can be expressed by numerical values that can be easily synthesized. Thus, the essence of the basic concept lies in the usage of numerical values that can be synthesized as the input parameters related to the constituent materials.

Here, the present inventors focused on a characteristic value of a constituent material as a parameter that can be expressed by a numerical value as an input parameter related to the constituent material.

Namely, the basic concept according to the present embodiment is one in which the value of physical quantity for the composite material is estimated by using the approximate function generated based on the characteristic values (numerical values) of the constituent materials constituting the composite material and the blending ratio of the constituent materials.

According to this basic concept, using the approximate function generated based on the characteristic values of the constituent materials and the blending ratio of the constituent materials makes it possible to obtain the following effects.

For example, in the approximate function generated based on the material names of the constituent materials and the blending ratio of the constituent materials as in the related technique, the input parameters are the material names of the constituent materials and the blending ratio of the constituent materials. Therefore, in a case where a new constituent material not used to generate the approximate function is contained in the composite material which becomes the evaluation target, the concept of the synthesizing operation between the material names of the constituent materials used when generating the approximate function and the material name of the new constituent material would not make sense. Thus, estimation accuracy of the value of physical quantity for the composite material is reduced. Namely, the approximate function generated in the related technique has a narrower range of application for the composite material in which the value of physical quantity can be estimated with high accuracy.

In particular, in the related technique, even if the material name of the new constituent material (new material name) not used to generate the approximate function is known, if the value of the corresponding physical quantity is not known, the physical quantity for the composite material which becomes the evaluation target cannot be estimated with high accuracy in the approximate function generated in the related technique. In other words, in the approximate function generated in the related technique, the physical quantity can be estimated with high accuracy only for the composite material containing only constituent materials used for the teacher data.

In contrast, in the basic concept according to the present embodiment, the approximate function is generated based on the characteristic values of the constituent materials and the blending ratio of the constituent materials. In this case, even if a new constituent material not used to generate the approximate function is contained in the composite material which becomes the evaluation target, if the characteristic value corresponding to this new constituent material is known, the value of physical quantity for the composite material can be estimated with high accuracy. This is because the characteristic values of the constituent materials can be expressed by numerical values, making it possible to perform the synthesizing operation.

Thus, the approximate function generated in the basic concept has a wider range of application than that of the approximate function generated in the related technique, and even if a new constituent material not used for the teacher data is contained in the composite material which becomes the evaluation target, there is a great technical significance in that the physical quantity for the composite material can be estimated with high accuracy. Namely, it can be said that the basic concept is an excellent technical concept in that, while the range of application of the approximate function generated in the related technique is limited to a range of the teacher data, the range of application of the approximate function generated in the basic concept is not limited to the range of the teacher data. For example, according to the basic concept, by accumulating the characteristic value for the new constituent material not used to generate the approximate function as a database, the physical quantity for the composite material containing the new constituent material not considered when generating the approximate function can be estimated with high accuracy. Further, the range of application of the approximate function generated in the basic concept is large in that, by using the approximate function according to the basic concept, even if the new constituent material is not accumulated in the database, if the characteristic value of the new constituent material can be obtained by some other means, the physical quantity for the composite material containing the new constituent material can be estimated with high accuracy.

Here, "characteristic value" refers to, for example, thermal characteristics, mechanical characteristics, physical characteristics, and the like. For example, thermal characteristics include heat of fusion, melt flow rate, and the like. In addition, physical characteristics include specific gravity. On the other hand, "physical quantity" refers to elongation, tensile, and the like.

In the present specification, "characteristic value" and "value of physical quantity" are used with clear distinction. Specifically, "characteristic value" refers to a parameter used to generate the approximate function and used as the input for the approximate function. On the other hand, "value of physical quantity" refers to a value output from the approximate function, and is a target value to be estimated by the physical quantity estimating system according to the present embodiment.

Hereinafter, an example in which the physical quantity estimating system embodying the basic concept is configured by a single computer will be mainly described. However, the physical quantity estimating system according to the present embodiment can be realized by a distributing system constituted by a plurality of computers.

<Configuration of Physical Quantity Estimating Apparatus>

<<Hardware Configuration>>

First, a hardware configuration of the physical quantity estimating apparatus according to the present embodiment will be described.

FIG. 1 is a drawing showing an example of a hardware configuration of a physical quantity estimating apparatus 100 according to the present embodiment. Note that the configuration shown in FIG. 1 is only an example of the hardware configuration of the physical quantity estimating apparatus 100. The hardware configuration of the physical quantity estimating apparatus 100 is not limited to the configuration shown in FIG. 1 and may have a different configuration.

In FIG. 1, the physical quantity estimating apparatus 100 comprises a central processing unit (CPU) 101 configured to execute a program. This CPU 101 is electrically connected to, for example, a read-only memory (ROM) 102, a random-access memory (RAM) 103, and a hard disk device 112 via a bus 113, and is configured to control these hardware devices.

In addition, the CPU 101 is also connected to an input device and an output device via the bus 113. Examples of the input device include a keyboard 105, a mouse 106, a communication board 107, a scanner 111, and the like. On the other hand, examples of the output device include a display 104, the communication board 107, a printer 110, and the like. Further, the CPU 101 may be connected to, for example, a removable disk device 108 or a CD/DVD-ROM device 109.

The physical quantity estimating apparatus 100 may be connected to, for example, a network. For example, in a case where the physical quantity estimating apparatus 100 is connected to another external device via the network, the communication board 107 partially constituting the physical quantity estimating apparatus 100 is connected to a local area network (LAN), a wide area network (WAN), or the Internet.

The RAM 103 is an example of a volatile memory, and recording mediums of the ROM 102, the removable disk device 108, the CD/DVD-ROM device 109, and the hard disk device 112 are examples of a non-volatile memory. A storage device of the physical quantity estimating apparatus 100 is constituted by these volatile and non-volatile memories.

The hard disk device 112 is configured to store, for example, an operating system (OS) 201, a program group 202, and a file group 203. The CPU 101 uses the operating system 201 to execute a program included in the program group 202. In addition, the RAM 103 is configured to temporarily store, for example, at least a part of a program of the operating system 201 and an application program to be executed by the CPU 101, and to also store various types of data necessary for processing by the CPU 101.

The ROM 102 is configured to store a basic input/output system (BIOS) program, and the hard disk device 112 is configured to store a boot program. When the physical quantity estimating apparatus 100 is started, the BIOS program stored in the ROM 102 and the boot program stored in the hard disk device 112 are executed, and the operating system 201 is started by the BIOS program and the boot program.

The program group 202 is configured to store programs that realize functions of the physical quantity estimating apparatus 100. These programs are read out and executed by the CPU 101. In addition, the file group 203 is configured to store information, data, signal values, variable values, and parameters indicating results of processing by the CPU 101 as each item in a file.

The file is recorded in a recording medium of the hard disk device 112, memories, or the like. The information, data, signal values, variable values, or parameters recorded in the recording medium of the hard disk device 112, memories, or the like are read out by the CPU 101 to a main memory or a cache memory, and are used for an operation of the CPU 101 such as extraction, search, reference, comparison, calculation, processing, editing, output, printing, and displaying. For example, during the operation of the above-described CPU 101, the information, data, signal values, variable values, and parameters are temporarily stored in the main memory, a register, the cache memory, a buffer memory, or the like.

Functions of the physical quantity estimating apparatus 100 may be realized by firmware stored in the ROM 102, or may be realized by software only, by hardware only such as an element, a device, a board, and wirings, by a combination of software and hardware, or by a combination with these and firmware. The firmware and the software are recorded as programs in the recording medium such as the hard disk device 112, a removable disk, a CD-ROM, a DVD-ROM, or the like. The programs are read out and executed by the CPU 101. Namely, the programs cause a computer to serve as the physical quantity estimating apparatus 100.

Thus, the physical quantity estimating apparatus 100 is a computer comprising the CPU 101 which is a processing device, the hard disk device 112 and the memories which are storage devices, the keyboard 105, the mouse 106, and the communication board 107 which are input devices, and the display 104, the printer 110, and the communication board 107 which are output devices. The functions of the physical quantity estimating apparatus 100 are realized by using the processing device, the storage devices, the input devices, and the output devices.

<<Functional Block Configuration>>

Next, a functional block configuration of the physical quantity estimating apparatus 100 will be described.

Figure 2:
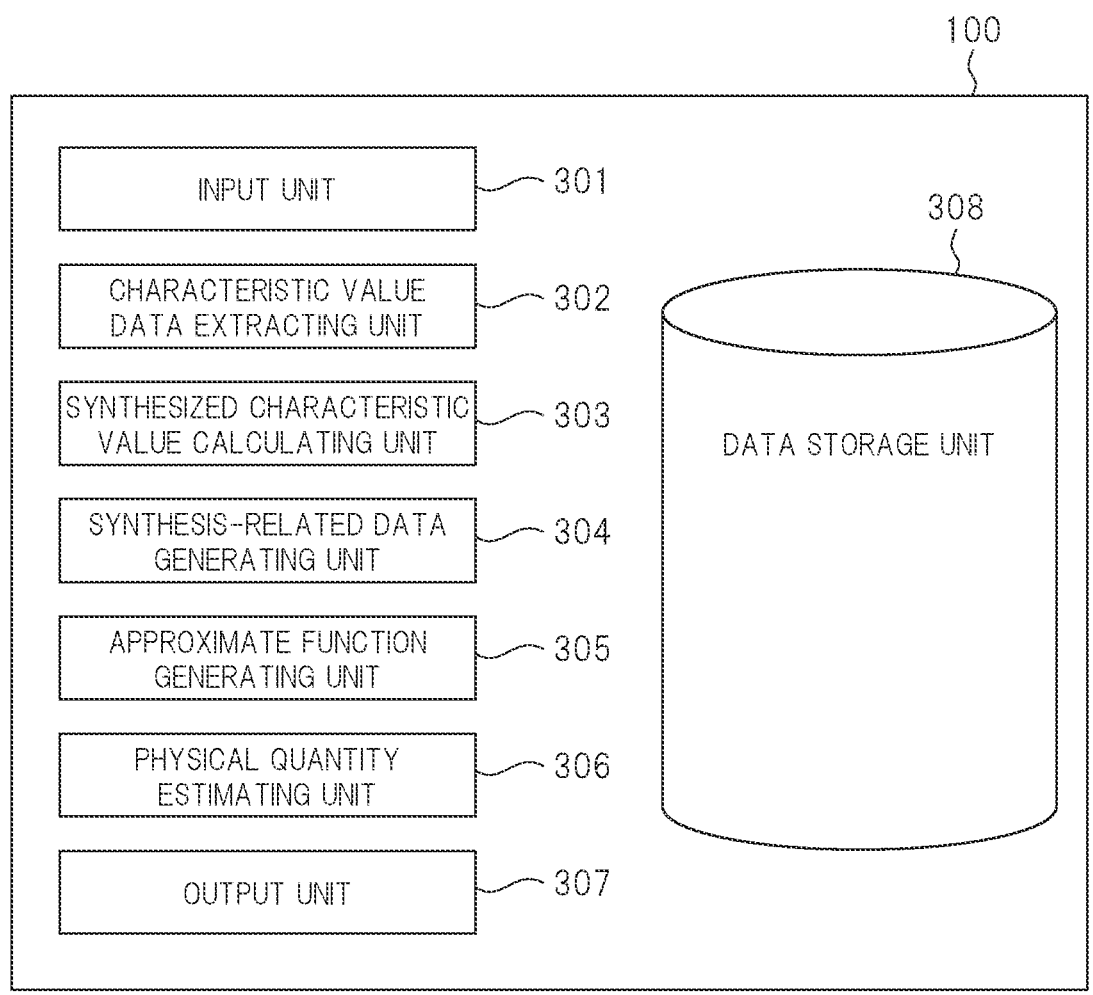
FIG. 2 is a functional block diagram showing functions of the physical quantity estimating apparatus.

FIG. 2 is a functional block diagram showing functions of the physical quantity estimating apparatus.

The physical quantity estimating apparatus 100 has an input unit 301, a characteristic value data extracting unit 302, a synthesized characteristic value calculating unit 303, a synthesis-related data generating unit 304, an approximate function generating unit 305, a physical quantity estimating unit 306, an output unit 307, and a data storage unit 308.

The input unit 301 is configured to input characteristic value data. Here, "characteristic value data" refers to data in which a material name and a characteristic value of the material are associated with each other for each of the plurality of different materials. The characteristic value data input by the input unit 301 is stored in the data storage unit 308. This data storage unit 308 serves as a database for storing a plurality of characteristic value data.

In addition, the input unit 301 is configured to input a blending data and a physical quantity data of a composite material containing two or more materials belonging to the plurality of different materials as constituent materials. Here, "blending data" refers to data including the material names and the blending ratio of the constituent materials constituting the composite material, and may also be referred to as blending information. On the other hand, "physical quantity data" refers to data indicating the value of physical quantity for the composite material whose value of physical quantity is known, and is, for example, data obtained through experiments. The blending data and the physical quantity data input by the input unit 301 are also stored in the data storage unit 308.

The characteristic value data extracting unit 302 is configured to extract characteristic value data corresponding to the constituent material contained in the composite material from the plurality of characteristic value data stored in the data storage unit 308. For example, in a case where the constituent materials contained in the composite material are "polyolefin" and "polyethylene", the characteristic value data extracting unit 302 is configured to extract characteristic value data corresponding to "polyolefin" and characteristic value data corresponding to "polyethylene" from the plurality of characteristic value data.

The synthesized characteristic value calculating unit 303 is configured to perform an operation of synthesizing the characteristic values corresponding to the constituent materials constituting the composite material based on the blending ratio included in the blending data input by the input unit 301 and the characteristic value included in the characteristic value data extracted by the characteristic value data extracting unit 302 to calculate a synthesized characteristic value of the composite material.

For example, it is considered that the composite material contains, as the constituent materials of the composite material, a constituent material with a characteristic value "50" and a constituent material with a characteristic value "75", and has the blending ratio of the constituent materials of 50:50. In this case, the synthesized characteristic value calculating unit 303 performs a synthesizing operation of "50"×0.5+"75"×0.5="62.5" to obtain the synthesized characteristic value of "62.5".

Examples of the synthesized characteristic value include synthesized heat of fusion of the composite material, synthesized melt flow rate of the composite material, and the like.

The synthesis-related data generating unit 304 is configured to generate synthesis-related data in which the synthesized characteristic value calculated by the synthesized characteristic value calculating unit 303 and the value of physical quantity for the composite material ("physical quantity data" of the composite material) are associated with each other. Generation of this synthesis-related data is performed for the composite material input by the input unit 301 and in which the corresponding physical quantity is known. For example, in a case of the above-described example in which the value of physical quantity for the composite material is "150", the synthesis-related data generating unit 304 generates the synthesis-related data in which the synthesized characteristic value "62.5" and the value of physical quantity "150" are associated with each other. The generated synthesis-related data is stored in the data storage unit 308.

The approximate function generating unit 305 has a function to generate an approximate function based on the synthesis-related data generated by the synthesis-related data generating unit 304. In other words, the approximate function generating unit 305 is configured to generate the approximate function in which the synthesized characteristic value and the value of physical quantity are associated with each other.

Figure 3:
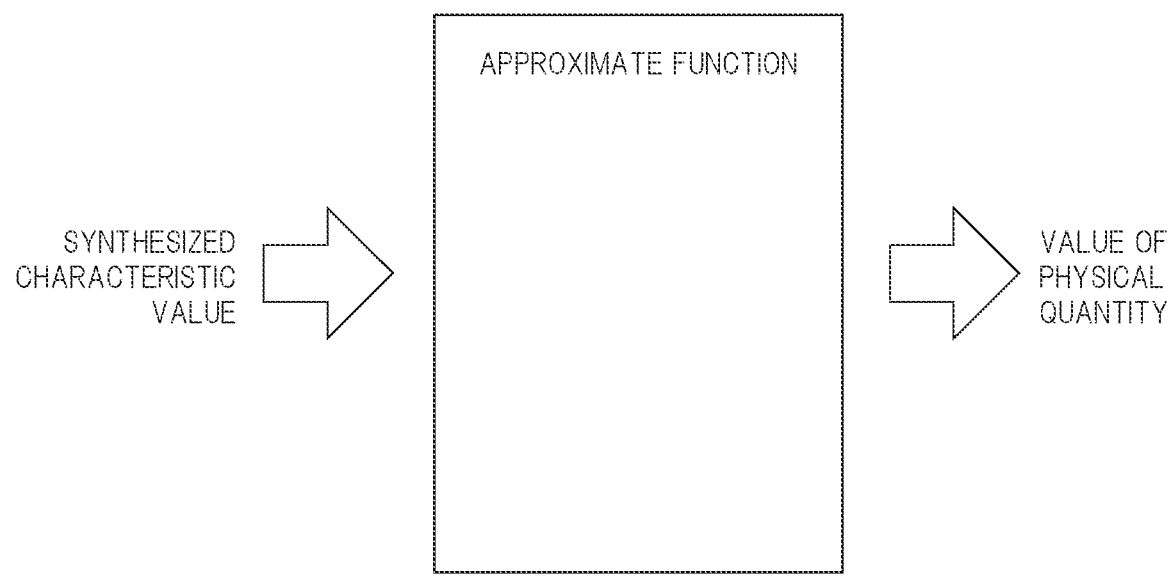
FIG. 3 is a drawing for describing machine learning for generating an approximate function.

Specifically, as shown in FIG. 3, the approximate function generating unit 305 is configured to generate the approximate function in which the synthesis-related data is used for the teacher data, the input is the synthesized characteristic value, and the output is the value of physical quantity.

Here, "approximate function" is defined as a function for outputting, when the synthesized characteristic value is input, the value of physical quantity corresponding to this synthesized characteristic value. Namely, "approximate function" is defined as a function for outputting, in a case where the synthesized characteristic value of the composite material whose correspondence to the value of physical quantity is unknown is input, the value of physical quantity that is presumed to be realized for this composite material. Thus, the approximate function can be said to be a function used to estimate the value of physical quantity for the composite material whose correspondence to the value of physical quantity is unknown.

The physical quantity estimating unit 306 is configured to estimate, based on a first synthesized characteristic value calculated by the synthesized characteristic value calculating unit 303 and on the approximate function generated by the approximate function generating unit 305, the value of physical quantity corresponding to a first composite material. The first synthesized characteristic value is calculated by the synthesized characteristic value calculating unit 303 based on a first blending ratio included in first blending data of the first composite material and on a characteristic value of first characteristic value data extracted by the characteristic value data extracting unit 302.

Note that "first composite material" refers to a composite material containing two or more materials belonging to the plurality of different materials as constituent materials, and is a composite material which becomes the evaluation target whose value of the corresponding physical quantity is unknown. Here, the blending data of the first composite material is referred to as "first blending data", and the blending ratio included in the blending data of the first composite material is referred to as "first blending ratio". In addition, the synthesized characteristic value of the first composite material is referred to as "first synthesized characteristic value", and among the characteristic value data stored in the data storage unit 308, the characteristic value data corresponding to the constituent material contained in the first composite material is referred to as "first characteristic value data".

For example, the first blending data is input from the input unit 301 to the physical quantity estimating apparatus 100, and the first characteristic value data is extracted by the characteristic value data extracting unit 302.

The output unit 307 outputs the value of physical quantity estimated by the physical quantity estimating unit 306.

The physical quantity estimating apparatus 100 is configured in such a manner.

Examples of the constituent materials of the composite material include a plurality of different types of resins, but may also include other constituent materials. For example, the constituent materials of the composite material may include an additive, an antioxidant, a cross-linking aid, or the like. In addition, an example of resin can include cross-linked resin. Specific constituent materials of the composite material may add additional functions to the physical quantity estimating apparatus 100. This will be described below.

<<<Composite Material Containing Additive>>>

In a case where the composite material contains an additive, the synthesized characteristic value calculating unit 303 is configured to further calculate an average inter-filler distance of the additive or a volume fraction of the additive based on a characteristic value of the additive, in addition to performing the above-described functions. The synthesized characteristic value calculated by the synthesized characteristic value calculating unit 303 includes the average inter-filler distance of the additive or the volume fraction of the additive.

Note that an average inter-particle distance such as the average inter-filler distance is calculated from, for example, an average particle size D50 using a theoretical formula. In addition, the volume fraction is calculated from the specific gravity of the compounded material.

<<<Composite Material Containing Antioxidant and Cross-Linking Aid>>>

In a case where the composite material contains an antioxidant and a cross-linking aid, the synthesized characteristic value calculating unit 303 is configured to further calculate a reaction molarity of a primary reaction group of the antioxidant, a reaction molarity of a secondary reaction group of the antioxidant, and a reaction molarity of the cross-linking aid based on a characteristic value of the antioxidant and on a characteristic value of the cross-linking aid, in addition to performing the above-described functions. The synthesized characteristic value calculated by the synthesized characteristic value calculating unit 303 includes the reaction molarity of the primary reaction group of the antioxidant, the reaction molarity of the secondary reaction group of the antioxidant, and the reaction molarity of the cross-linking aid.

<<<Composite Material Containing Cross-Linked Resin>>>

In a case where the composite material contains cross-linked resin, the input unit 301 is configured to further input a radiation dose for cross-linking the resin. The approximate function generating unit 305 is configured to generate the approximate function based on the synthesis-related data and the radiation dose. The approximate function in this case is generated as a function in which the inputs are the synthesized characteristic value and the radiation dose, and the output is the value of physical quantity. In addition, the physical quantity estimating unit 306 is configured to estimate the value of physical quantity for the first composite material based on the first synthesized characteristic value, the first radiation dose, and the approximate function. Here, "first radiation dose" refers to a radiation dose applied to the first composite material.

<Operation of Physical Quantity Estimating Apparatus>

The physical quantity estimating apparatus 100 according to the present embodiment is configured as described above, and hereinafter, its operation will be described. The operation of the physical quantity estimating apparatus 100 includes an "operation of generating the operation of generating the approximate function" and an "operation of estimating the value of physical quantity corresponding to the composite material of the evaluation target". Hereinafter, these operations will be described.

<<Operation of Generating Approximate Function>>

Figure 4:
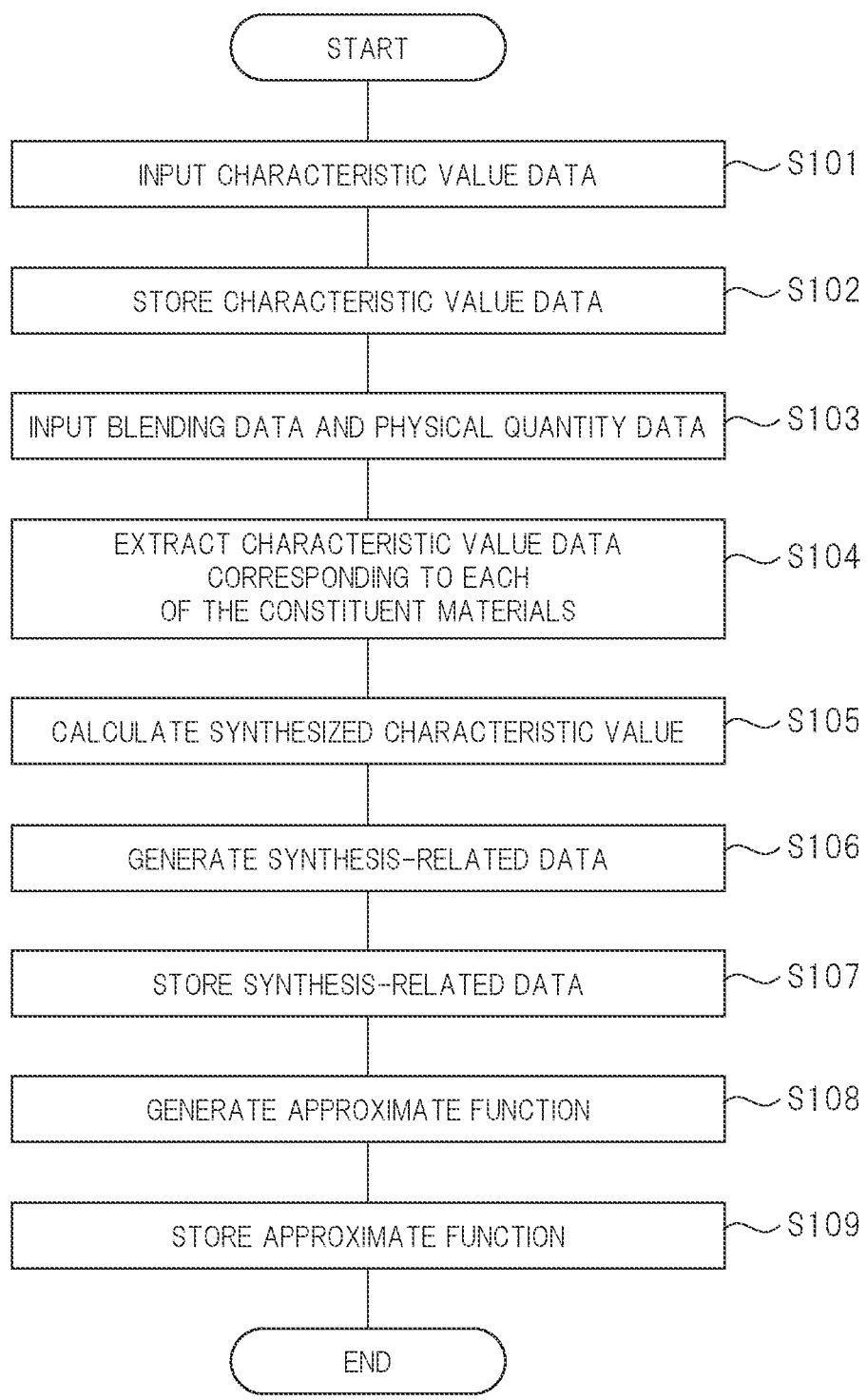
FIG. 4 is a flowchart for describing an operation of generating the approximate function.

FIG. 4 is a flowchart for describing the operation of generating the approximate function.

In FIG. 4, first, the input unit 301 inputs a plurality of characteristic value data in which a material name and the characteristic value of the material are associated with each other for each of the plurality of different materials (S101). The plurality of characteristic value data input by the input unit 301 are then stored in the data storage unit 308 (S102).

Next, the input unit 301 inputs the blending data and the physical quantity data of the composite material containing two or more materials as constituent materials and whose value of the corresponding physical quantity is known (S103).

Subsequently, the characteristic value data extracting unit 302 extracts the characteristic value data corresponding to the constituent material contained in the composite material from the plurality of characteristic value data stored in the data storage unit 308 (S104). Next, the synthesized characteristic value calculating unit 303 performs the operation of synthesizing the characteristic values of the characteristic value data extracted by the characteristic value data extracting unit based on the blending data input by the input unit 301 to calculate the synthesized characteristic value of the composite material (S105).

The synthesis-related data generating unit 304 then generates the synthesis-related data in which the synthesized characteristic value calculated by the synthesized characteristic value calculating unit 303 and the value of physical quantity (physical quantity data) for the composite material are associated with each other (S106). Subsequently, the synthesis-related data generated by the synthesis-related data generating unit 304 is stored in the data storage unit 308 (S107).

Next, the approximate function generating unit 305 generates the approximate function based on the synthesis-related data generated by the synthesis-related data generating unit 304 (S108). Specifically, the approximate function generating unit 305 generates the approximate function in which the synthesis-related data is used for the teacher data, the input is the synthesized characteristic value, and the output is the value of physical quantity (see FIG. 3).

The approximate function generated by the approximate function generating unit 305 is then stored in the data storage unit 308 (S109). In this manner, the operation of generating the approximate function is performed.

<<Operation of Estimating Value of Physical Quantity for First Composite Material of Evaluation Target>>

Next, an operation of estimating a value of physical quantity for the first composite material of the evaluation target will be described.

Figure 5:
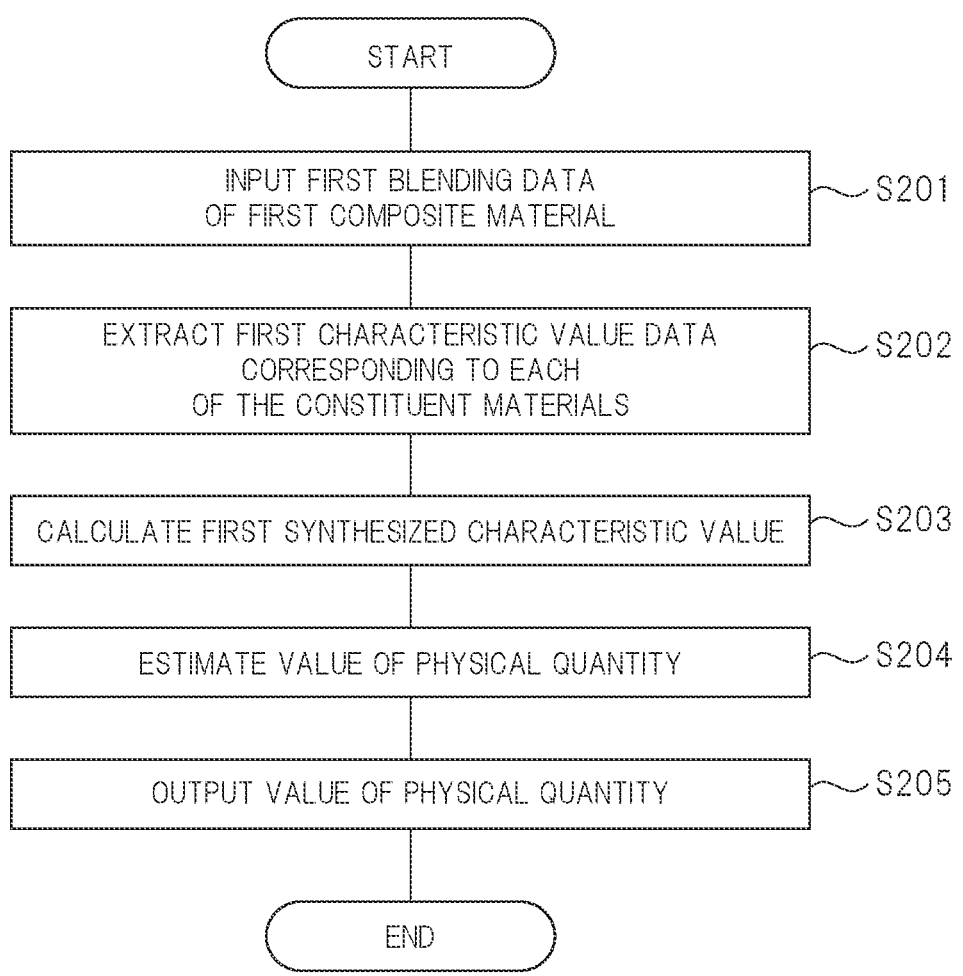
FIG. 5 is a flowchart for describing an operation of estimating a value of physical quantity for a composite material of an evaluation target.

FIG. 5 is a flowchart for describing the operation of estimating the value of physical quantity for the first composite material of the evaluation target. Note that the approximate function is already stored in the data storage unit 308.

In FIG. 5, first, the input unit 301 inputs the first blending data of the first composite material which becomes the evaluation target whose correspondence to the value of physical quantity is unknown (S201).

Next, the characteristic value data extracting unit 302 extracts the first characteristic value data corresponding to the constituent material contained in the first composite material from the plurality of characteristic value data stored in the data storage unit 308 (S202).

Next, the synthesized characteristic value calculating unit 303 performs the operation of synthesizing the characteristic values of the first characteristic value data extracted by the characteristic value data extracting unit 302 based on the first blending data input by the input unit 301 to calculate the first synthesized characteristic value of the first composite material (S203).

Subsequently, the physical quantity estimating unit 306 inputs the first synthesized characteristic value calculated by the synthesized characteristic value calculating unit 303 to the approximate function to estimate the value of physical quantity for the first composite material (S204). The output unit 307 then outputs the value of physical quantity estimated by the physical quantity estimating unit 306 (S205). In this manner, the physical quantity estimating apparatus 100 makes it possible to output the value of physical quantity that is highly likely to be realized for the first composite material which becomes the evaluation target whose correspondence to the value of physical quantity is unknown.

<Physical Quantity Estimating Program>

The physical quantity estimating method performed by the above-described physical quantity estimating apparatus 100 can be realized by a physical quantity estimating program that causes the computer to execute a physical quantity estimating process.

For example, in the physical quantity estimating apparatus 100 constituted by the computer shown in FIG. 1, the physical quantity estimating program according to the present embodiment can be introduced as one program group 202 stored in the hard disk device 112. The computer which is the physical quantity estimating apparatus 100 executes the physical quantity estimating program to realize the physical quantity estimating method according to the present embodiment.

The physical quantity estimating program that causes the computer to execute each process for creating data related to the physical quantity estimating process can be recorded and distributed on a computer-readable recording medium. Examples of the recording medium include a magnetic storage medium such as a hard disk or a flexible disk, an optical storage medium such as a CD-ROM or a DVD-ROM, a hardware device such as a non-volatile memory including a ROM or an EEPROM, or the like.

Modification Example

In the embodiment, as shown in FIG. 2, an example in which the physical quantity estimating system configured to estimate the value of physical quantity for the composite material is constituted by a single physical quantity estimating apparatus 100 has been described. However, the physical quantity estimating system is not limited to such a configuration, and can be constituted by, for example, the distributing system.

Figure 6:
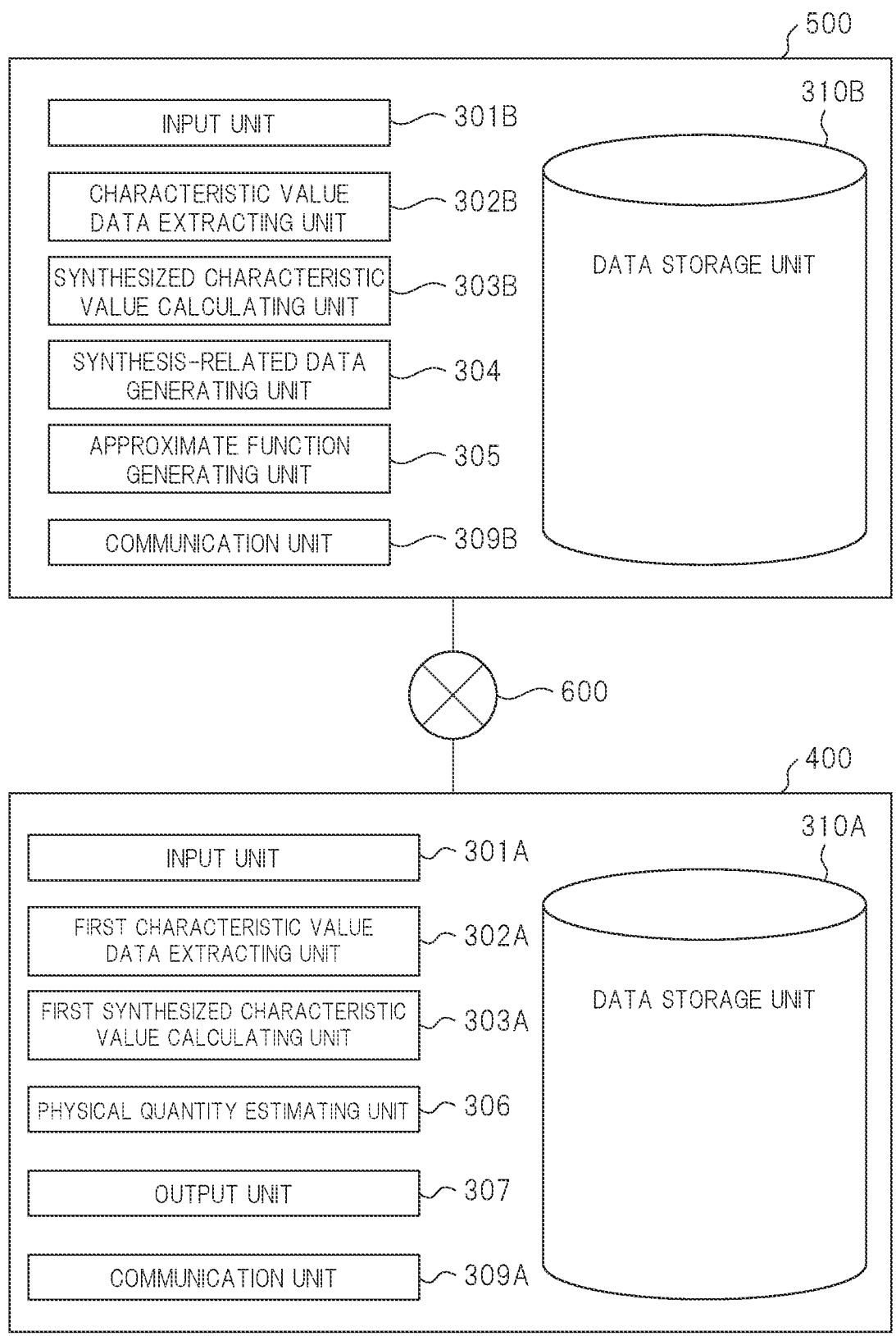
FIG. 6 is a functional block diagram showing an example in which a physical quantity estimating system is constituted by the physical quantity estimating apparatus and an approximate function generating apparatus.

FIG. 6 is a functional block diagram showing an example in which the physical quantity estimating system is constituted by the physical quantity estimating apparatus and an approximate function generating apparatus.

As shown in FIG. 6, the physical quantity estimating system is constituted by a physical quantity estimating apparatus 400 and an approximate function generating apparatus 500, and, for example, the physical quantity estimating apparatus 400 and the approximate function generating apparatus 500 are connected by a network 600.

The physical quantity estimating apparatus 400 has an input unit 301A, a first characteristic value data extracting unit 302A, a first synthesized characteristic value calculating unit 303A, the physical quantity estimating unit 306, the output unit 307, a communication unit 309A, and a data storage unit 310A.

The approximate function generating apparatus 500 has an input unit 301B, a characteristic value data extracting unit 302B, a synthesized characteristic value calculating unit 303B, the synthesis-related data generating unit 304, the approximate function generating unit 305, a communication unit 309B, and a data storage unit 310B.

The physical quantity estimating apparatus 400 and the approximate function generating apparatus 500 configured in such a manner are configured such that data can be sent and received by the communication unit 309A and the communication unit 309B via the network 600. In the approximate function generating apparatus 500, the above-described "operation of generating the approximate function" is performed to generate the approximate function.

On the other hand, in the physical quantity estimating apparatus 400, the first synthesized characteristic value calculated by the first synthesized characteristic value calculating unit 303A is output to the approximate function generating apparatus 500. Subsequently, in the approximate function generating apparatus 500, an output result output from the approximate function by inputting the first synthesized characteristic value to the approximate function is input from the approximate function generating apparatus 500 and is stored in the data storage unit 310A.

Subsequently, in the physical quantity estimating apparatus 400, the value of physical quantity for the composite material of the above-described evaluation target is obtained based on the output result input from the approximate function generating apparatus 500.

In this manner, the physical quantity estimating system according to the present embodiment can be constructed by the distributing system comprising the physical quantity estimating apparatus 400 and the approximate function generating apparatus 500.

(Applied Concept in which Basic Concept is Applied)

In the above-described basic concept, for the first composite material whose value of physical quantity is unknown, the first synthesized characteristic value of the first composite material is calculated based on the first blending ratio of the first composite material and on the characteristic value corresponding to the constituent materials contained in the first composite material, and this calculated first synthesized characteristic value is input to the approximate function generated by the approximate function generating unit such that an output value output from the approximate function is estimated as the value of physical quantity for the first composite material.

In this case, even if a new constituent material not used for the teacher data is contained in the first composite material, the value of physical quantity for the first composite material can be estimated with high accuracy.

Namely, even if a new constituent material not used to generate the approximate function is contained in the first composite material, if the characteristic value corresponding to this new constituent material is known, the value of physical quantity for the first composite material can be estimated with high accuracy. This is because the characteristic values of the constituent materials are expressed by numerical values, making it possible to perform the synthesizing operation to calculate the first synthesized characteristic value (analog numerical value) for the first composite material.

Therefore, even if a new constituent material not used for the teacher data is contained in the first composite material which becomes the evaluation target, the basic concept has a great technical significance in that the value of physical quantity for the first composite material can be estimated with high accuracy.

In this regard, the present inventors made further improvements on the basic concept and devised a configuration in which the value of physical quantity for the first composite material whose value of physical quantity is unknown can be more accurately estimated. Hereinafter, the applied concept in which such an improvement is applied will be described.

<Applied Concept>

It is assumed in the applied concept that, when the first synthesized characteristic value of the first composite material whose value of physical quantity is unknown and the blending information including the material names and the blending ratio of the constituent materials contained in the first composite material are input, the approximate function for outputting the value of physical quantity for the first composite material is generated. The applied concept is a concept in which the value of physical quantity (objective variable) for the first composite material is estimated using the blending information of the constituent materials contained in the first composite material as the input parameter (explanatory variable) of the approximate function, in addition to using the first synthesized characteristic value calculated based on the first blending ratio of the constituent materials contained in the first composite material and on the characteristic value corresponding to the constituent materials contained in the first composite material. According to this applied concept, the value of physical quantity for the first composite material whose value of physical quantity is unknown can be estimated with an even higher high accuracy than in the basic concept.

This point is qualitatively described below.

For example, in a case where the input parameter is "x" and the output parameter is "y", the approximate function is represented by a function "f" where y=f(x). At this time, considering that the approximate function is generated by machine learning, the more types of input parameters "x" are used, the more accurate the obtained approximate function would generally become. Thus, the applied concept uses not only the first synthesized characteristic value but also the blending information including "material names" and "blending ratio" as the input parameters "x". This make it possible to provide more types of input parameters in the applied concept than in the basic concept where the only input parameter is the first synthesized characteristic value. As a result, it can be qualitatively understood that the applied concept makes it possible to generate the approximate function that is more accurate than in the basic concept.

Further, it is assumed that there are provided the first composite material and a second composite material whose values of physical quantity are unknown. Here, the first composite material is constituted by a constituent material A1, a constituent material A2, and a constituent material A3, while the second composite material is constituted by a constituent material B1, a constituent material B2, and a constituent material B3. At this time, it is considered to estimate the value of physical quantity using the basic concept.

In the first composite material, for example, it is assumed that the first synthesized characteristic value is calculated based on the blending ratio of the constituent materials A1 to A3 and on the characteristic value of each of the constituent materials A1 to A3. Inputting this first synthesized characteristic value to the approximate function makes it possible to obtain an estimate value of the physical quantity for the first composite material.

Likewise, for example, in the second composite material, it is assumed that a second synthesized characteristic value is calculated based on the blending ratio of the constituent materials B1 to B3 and on the characteristic value of each of the constituent materials B1 to B3. Inputting this second synthesized characteristic value to the approximate function makes it possible to obtain an estimate value of the physical quantity for the second composite material.

Here, for example, even if the first composite material and the second composite material are of different types, the first synthesized characteristic value of the first composite material and the second synthesized characteristic value of the second composite material are the same. In this case, in the basic concept, if the first synthesized characteristic value and the second synthesized characteristic value input to the approximate function are the same, the values of physical quantity output from the approximate function will be the same.

Therefore, even if the constituent materials (constituent materials A1 to A3) of the first composite material and the constituent materials (constituent materials B1 to B3) of the second composite material differ, in the basic concept, the value of physical quantity of the first composite material and the value of physical quantity of the second composite material are estimated to be the same value. This means that there exists room for improvement in the basic concept.

In contrast, the applied concept uses not only the first synthesized characteristic value and the second synthesized characteristic value but also the blending information including "material names" and "blending ratio" as the input parameters "x". Thus, for example, even if the first composite material and the second composite material are of different types, and even if the first synthesized characteristic value of the first composite material and the second synthesized characteristic value of the second composite material are the same, the blending information including "material name" and "blending ratio" of each of the constituent materials A1 to A3 and the blending information including "material name" and "blending ratio" of each of the constituent materials B1 to B3 would differ.

For this reason, in the applied concept, even if the first synthesized characteristic value of the first composite material and the second synthesized characteristic value of the second composite material are the same, each of the blending information including "material name" and "blending ratio" differs, whereby the value of physical quantity of the first composite material and the value of physical quantity of the second composite material are estimated to be different values. In other words, it is possible to avoid obtaining the same value for the estimated values of physical quantity even if the first composite material and the second composite material are of different types. This is one of the advantages of the applied concept.

From the above, it can be qualitatively understood that the applied concept makes it possible to estimate the value of physical quantity that is more accurate than in the basic concept.

Embodiment Embodying Applied Concept

Next, an embodiment embodying the applied concept will be described. For example, the physical quantity estimating apparatus 100 can be used in this embodiment embodying the applied concept.

<<<Configuration of Physical Quantity Estimating Apparatus>>>
<<<Hardware Configuration>>>

The hardware configuration of the physical quantity estimating apparatus 100 according to the present embodiment has a configuration similar to that shown in, for example, FIG. 1. Note that the configuration shown in FIG. 1 is only an example of the hardware configuration of the physical quantity estimating apparatus 100. The hardware configuration of the physical quantity estimating apparatus 100 is not limited to the configuration shown in FIG. 1 and may have a different configuration.

<<<Functional Block Configuration>>>

The present embodiment also uses the functional block configuration shown in FIG. 2.

The physical quantity estimating apparatus 100 according to the present embodiment also has the input unit 301, the characteristic value data extracting unit 302, the synthesized characteristic value calculating unit 303, the synthesis-related data generating unit 304, the approximate function generating unit 305, the physical quantity estimating unit 306, the output unit 307, and the data storage unit 308.

The input unit 301 is configured to input the characteristic value data. Here, "characteristic value data" refers to data in which the material name and the characteristic value of the material are associated with each other for each of the plurality of different materials. The characteristic value data input by the input unit 301 is stored in the data storage unit 308. This data storage unit 308 serves as a database for storing the plurality of characteristic value data.

In addition, the input unit 301 is configured to input the blending data and the physical quantity data of the composite material containing two or more materials belonging to the plurality of different materials as constituent materials.

Here, "blending data" refers to data including the material names and the blending ratio of the constituent materials constituting the composite material, and may also be referred to as blending information. On the other hand, "physical quantity data" refers to data indicating the value of physical quantity for the composite material whose value of physical quantity is known, and is, for example, data obtained through experiments. The blending data and the physical quantity data input by the input unit 301 are also stored in the data storage unit 308.

The characteristic value data extracting unit 302 is configured to extract the characteristic value data corresponding to the constituent material contained in the composite material from the plurality of characteristic value data stored in the data storage unit 308.

The synthesized characteristic value calculating unit 303 is configured to perform the operation of synthesizing the characteristic values corresponding to the constituent materials constituting the composite material based on the blending ratio included in the blending data input by the input unit 301 and on the characteristic value included in the characteristic value data extracted by the characteristic value data extracting unit 302 to calculate the synthesized characteristic value of the composite material.

The synthesis-related data generating unit 304 is configured to generate the synthesis-related data in which the synthesized characteristic value calculated by the synthesized characteristic value calculating unit 303 and the value of physical quantity for the composite material ("physical quantity data" of the composite material) are associated with each other. Generation of this synthesis-related data is performed for the composite material input by the input unit 301 and whose corresponding physical quantity is known.

The approximate function generating unit 305 has a function to generate the approximate function based on the synthesis-related data generated by the synthesis-related data generating unit 304 and on the blending information including the material names and the blending ratio input by the input unit 301. In other words, the approximate function generating unit 305 has a function to generate, when the first synthesized characteristic value of the first composite material whose value of physical quantity is unknown and the blending information including the material names and the blending ratio of the constituent materials contained in the first composite material are input, the approximate function for outputting the value of physical quantity for the first composite material. In other words, the approximate function generating unit 305 is configured to generate the approximate function in which the blending information, the synthesized characteristic value, and the value of physical quantity are associated with one another.

Figure 7:
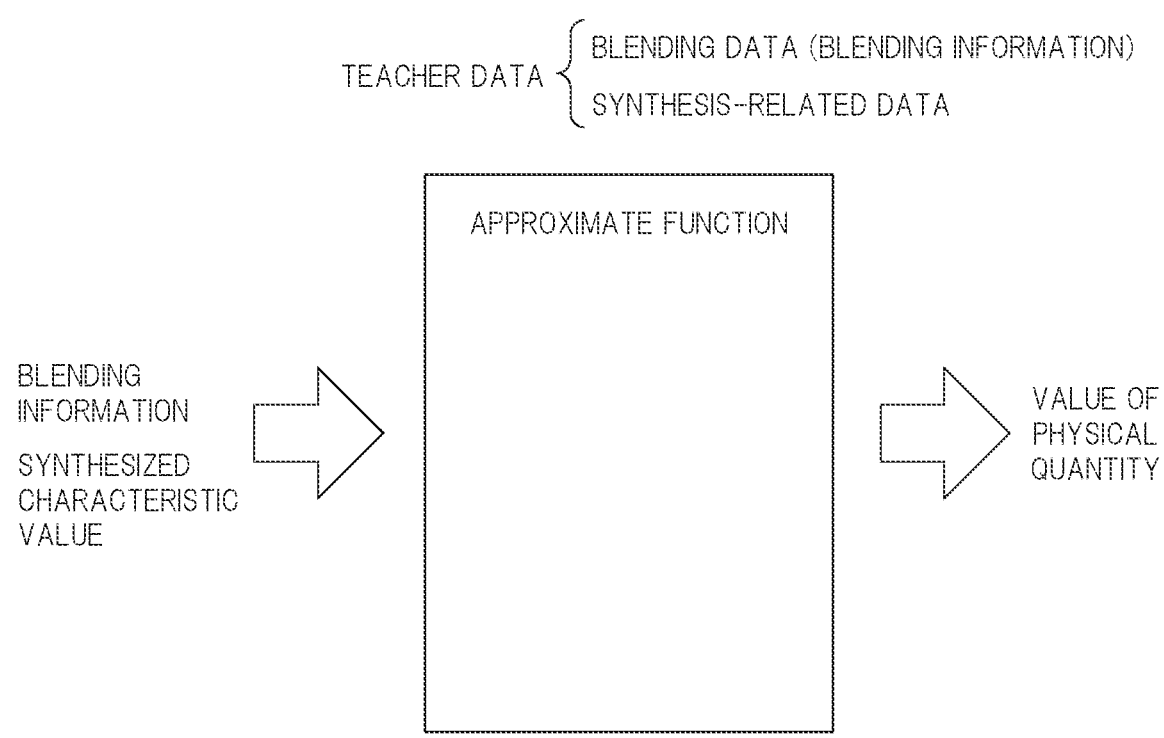
FIG. 7 is a drawing for describing machine learning for generating the approximate function.

Specifically, as shown in FIG. 7, the approximate function generating unit 305 is configured to generate the approximate function in which the blending data and the synthesis-related data are used for the teacher data, the inputs are the material names and the synthesized characteristic value, and the output is the value of physical quantity.

Here, "approximate function" is defined as a function for outputting, when the blending information and the synthesized characteristic value are input, the value of physical quantity corresponding to the blending information and the synthesized characteristic value. Namely, "approximate function" is defined as a function for outputting, in a case where the blending information of the constituent materials constituting the first composite material whose correspondence to the value of physical quantity is unknown and the synthesized characteristic value of the composite material are input, the value of physical quantity that is presumed to be realized by this first composite material.

Thus, the approximate function can be said to be a function used to estimate the value of physical quantity for the first composite material whose correspondence to the value of physical quantity is unknown.

The physical quantity estimating unit 306 is configured to estimate the value of physical quantity corresponding to the first composite material based on the first synthesized characteristic value calculated by the synthesized characteristic value calculating unit 303, the first blending data of the first composite material, and the approximate function generated by the approximate function generating unit 305. The first synthesized characteristic value is calculated by the synthesized characteristic value calculating unit 303 based on the first blending ratio included in the first blending data of the first composite material and on the characteristic value of the first characteristic value data extracted by the characteristic value data extracting unit 302.

The output unit 307 outputs the value of physical quantity estimated by the physical quantity estimating unit 306.

The physical quantity estimating apparatus 100 is configured in such a manner.

<<Operation of Physical Quantity Estimating Apparatus>>

<<<Operation of Generating Approximate Function>>>

Figure 8:
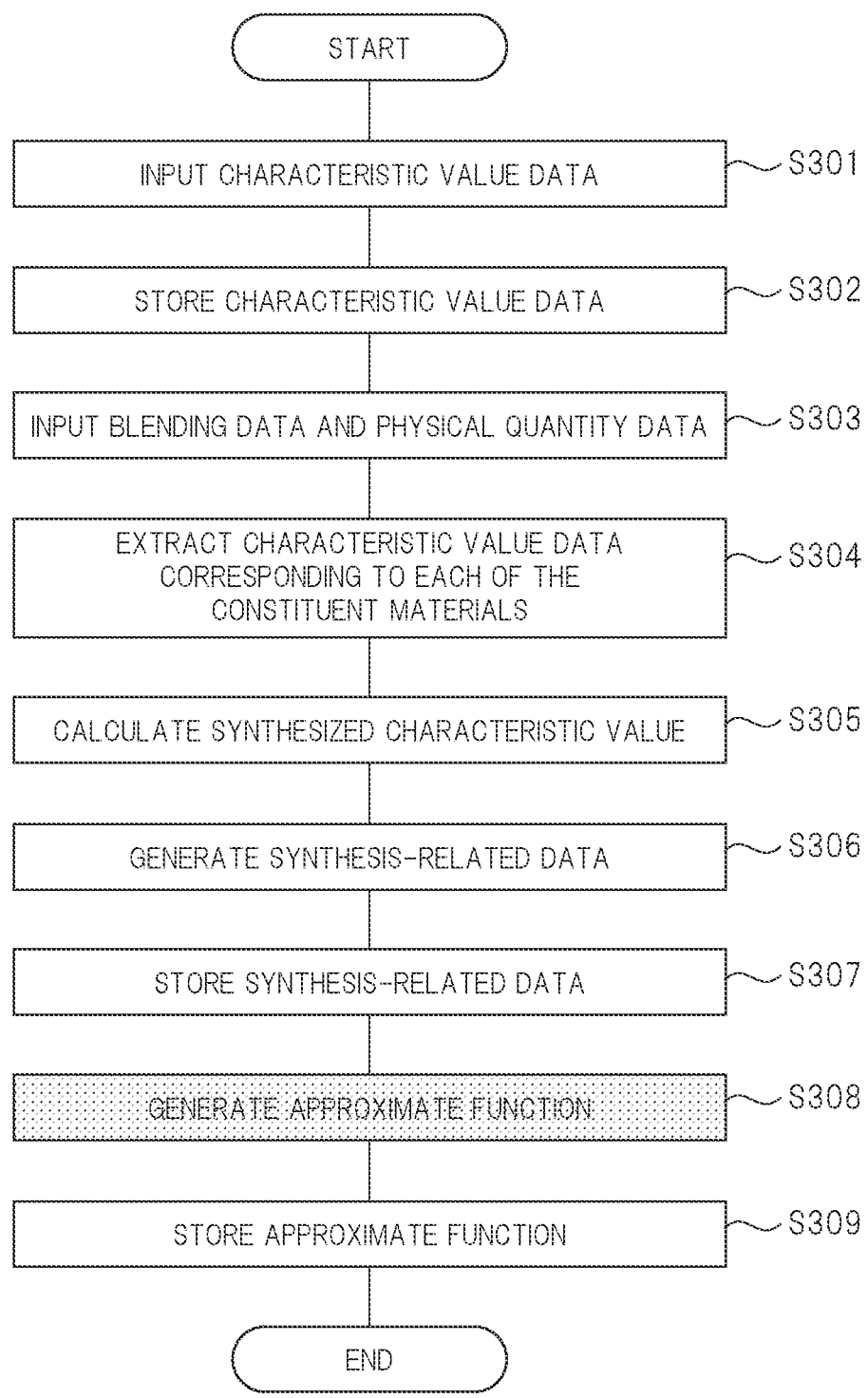
FIG. 8 is a flowchart for describing an operation of generating the approximate function.

FIG. 8 is a flowchart for describing the operation of generating the approximate function.

In FIG. 8, first, the input unit 301 inputs the plurality of characteristic value data in which the material name and the characteristic value of the material are associated with each other for each of the plurality of different materials (S301). The plurality of characteristic value data input by the input unit 301 are then stored in the data storage unit 308 (S302).

Next, the input unit 301 inputs the blending data and the physical quantity data of the composite material containing two or more materials as constituent materials and whose value of the corresponding physical quantity is known (S303).

Subsequently, the characteristic value data extracting unit 302 extracts the characteristic value data corresponding to the constituent material contained in the composite material from the plurality of characteristic value data stored in the data storage unit 308 (S304). Next, the synthesized characteristic value calculating unit 303 performs the operation of synthesizing the characteristic values of the characteristic value data extracted by the characteristic value data extracting unit based on the blending ratio included in the blending data input by the input unit 301. This allows the synthesized characteristic value calculating unit 303 to calculate the synthesized characteristic value of the composite material (S305).

The synthesis-related data generating unit 304 then generates the synthesis-related data in which the synthesized characteristic value calculated by the synthesized characteristic value calculating unit 303 and the value of physical quantity (physical quantity data) for the composite material are associated with each other (S306). Subsequently, the synthesis-related data generated by the synthesis-related data generating unit 304 is stored in the data storage unit 308 (S307).

Next, the approximate function generating unit 305 generates the approximate function based on the blending information (blending data) and the synthesis-related data generated by the synthesis-related data generating unit 304 (S308). Specifically, the approximate function generating unit 305 generates the approximate function in which the blending information and the synthesis-related data are used for the teacher data, the inputs are the blending information and the synthesized characteristic value, and the output is the value of physical quantity.

In this regard, the applied concept is characterized by the fact that the approximate function is generated using not only the synthesis-related data but also the blending information including the material names and the blending ratio for the teacher data, unlike the basic concept in which the approximate function is generated using only the synthesis-related data for the teacher data.

Thus, according to the applied concept, it is possible to generate a more accurate approximate function by providing more types of input parameters (explanatory variables) used at the time of machine learning.

The approximate function generated by the approximate function generating unit 305 is then stored in the data storage unit 308 (S309). In this manner, the operation of generating the approximate function is performed.

<<<Operation of Estimating Value of Physical Quantity for First Composite Material of Evaluation Target>>>

Next, the operation of estimating the value of physical quantity for the first composite material of the evaluation target will be described.

Figure 9:
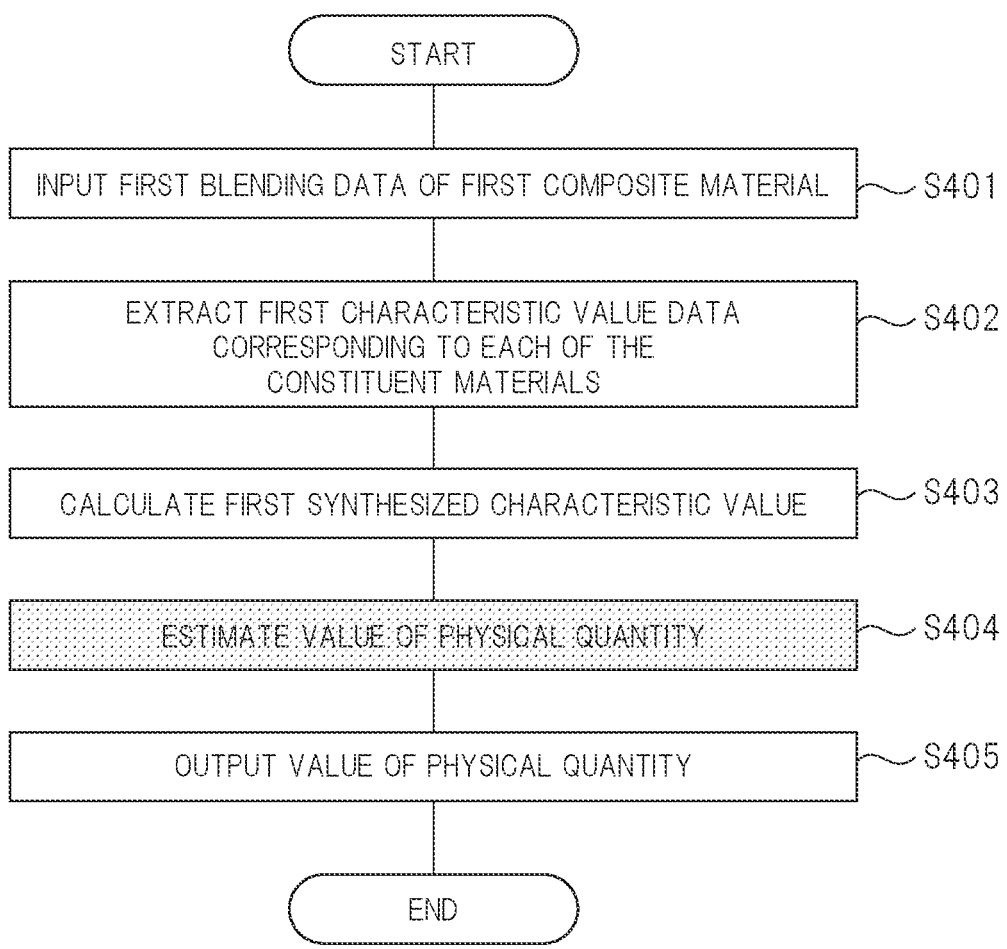
FIG. 9 is a flowchart for describing an operation of estimating the value of physical quantity for the composite material of the evaluation target.

FIG. 9 is a flowchart for describing the operation of estimating the value of physical quantity for the first composite material of the evaluation target. Note that the approximate function is already stored in the data storage unit 308.

In FIG. 9, first, the input unit 301 inputs the first blending data of the first composite material which becomes the evaluation target whose correspondence to the value of physical quantity is unknown (S401).

Next, the characteristic value data extracting unit 302 extracts the first characteristic value data corresponding to the constituent material contained in the first composite material from the plurality of characteristic value data stored in the data storage unit 308 (S402).

Next, the synthesized characteristic value calculating unit 303 performs the operation of synthesizing the characteristic values of the first characteristic value data extracted by the characteristic value data extracting unit 302 based on the first blending ratio included in the first blending data input by the input unit 301. Thus, the synthesized characteristic value calculating unit 303 calculates the first synthesized characteristic value of the first composite material (S403).

Subsequently, the physical quantity estimating unit 306 inputs both the first blending data and the first synthesized characteristic value calculated by the synthesized characteristic value calculating unit 303 to the approximate function to estimate the value of physical quantity for the first composite material (S404). The output unit 307 then outputs the value of physical quantity estimated by the physical quantity estimating unit 306 (S405).

In this manner, the physical quantity estimating apparatus 100 makes it possible to output the value of physical quantity that is highly likely to be realized for the first composite material which becomes the evaluation target whose correspondence to the value of physical quantity is unknown.

In particular, the applied concept uses not only the first synthesized characteristic value but also the blending information including the material names and the blending ratio of the constituent materials as the input parameters for the approximate function, and differs from the basic concept that uses only the first synthesized characteristic value as the input parameter for the approximate function.

As a result, according to the applied concept, it is possible to improve estimation accuracy of the value of physical quantity by providing more types of input parameters for the approximate function.

Specific Example

Next, a specific example embodying the applied concept will be described.

FIG. 10 is a table showing data in which the blending data and the physical quantity data are combined according to the specific example. In FIG. 10, a blending number is an ID number for identifying the composite material. Further, in FIG. 10, the constituent materials constituting the composite material include resins, flame retardants (fillers), antioxidants, lubricants, a coloring agent, and a cross-linking aid.

The resins are indicated by the material names of resin A, resin B, resin C, resin D, resin E, resin F, and resin G. In addition, the flame retardants are indicated by the material names of flame retardant H, flame retardant I, and flame retardant J. Further, the antioxidants are indicated by the material names of antioxidant K and antioxidant L, and the lubricants are indicated by the material names of lubricant M, lubricant N, and lubricant O. In addition, the coloring agent is indicated by the material name of coloring agent P, and the cross-linking aid is indicated by the material name of cross-linking aid Q.

In FIG. 10, for example, the composite material identified by the blending number "ID1" contains, as constituent materials, the resin B (20 parts by mass), the resin C (50 parts by mass), the resin E (30 parts by mass), the flame retardant H (200 parts by mass), the antioxidant K (1 part by mass), the antioxidant L (2 parts by mass), the lubricant M (1 part by mass), the lubricant N (2 parts by mass), the coloring agent P (2 parts by mass), and the cross-linking aid Q (4 parts by mass). Thus, it can be seen that the data shown in FIG. 10 includes the blending data (blending information) including the material names and the blending ratio of the constituent materials constituting the composite material.

Further, in FIG. 10, for example, the composite material identified by the blending number "ID1" is shown to have a tensile strength of "8.3347" as the physical quantity. Namely, the data shown in FIG. 10 also includes the physical quantity data indicating the value of physical quantity for the composite material whose value of physical quantity is known. From the above, it can be seen that FIG. 10 includes a combination of the blending data and the physical quantity data for the composite material whose value of physical quantity is known.

Next, in the specific example, data shown in FIG. 11 is generated based on the data shown in FIG. 10 which includes the blending data and the physical quantity data. This data shown in FIG. 11 is constituted by the synthesis-related data, supplementary data, and additional data. Here, the synthesis-related data refers to data in which the synthesized characteristic value and the value of physical quantity (physical quantity data) for the composite material are associated with each other. In addition, the supplementary data refers to data in which a value of a categorical variable and the value of physical quantity (physical quantity data) for the composite material are associated with each other, and the additional data refers to data in which an irradiation dose as a process condition value and the value of physical quantity (physical quantity data) for the composite material are associated with each other.

First, the synthesis-related data included in the data shown in FIG. 11 will be described.

The synthesized characteristic value included in the synthesis-related data is calculated by performing the operation of synthesizing the characteristic values of the characteristic value data based on the blending ratio included in the blending data in the data shown in FIG. 10 and the characteristic value data (not shown). Here, the characteristic value data refers to data in which the material name and the characteristic value of the material are associated with each other for each of the plurality of different materials, and is data obtained in advance. For example, when focusing on the resin A shown in FIG. 10, the characteristic value data can refer to data in which the material name "resin A" and the characteristic value of the resin A are associated with each other.

Here, the synthesized characteristic values do not necessarily have to be synthesized using the characteristic values for all of the constituent materials constituting the composite material, but may be synthesized using only the characteristic values for some of the constituent materials constituting the composite material (limited to the relevant constituent materials).

Hereinafter, the synthesized characteristic value will be described in detail.

In FIG. 11, the synthesized characteristic value of the specific example includes five types of synthesized characteristic values. Hereinafter, the five types of synthesized characteristic values will be described.

(1) Filler Volume Ratio

A filler volume ratio refers to a ratio of a volume of the filler (flame retardant) to a volume of the resin (base polymer), and is a parameter indicating how much of the filler is added to the resin. For example, the synthesized characteristic value regarding the filler volume ratio is related to the resin and the filler. Thus, an operation of calculating the synthesized characteristic value is performed based on the characteristic value of each of the resins (resins A to G) shown in FIG. 10 and the characteristic value of each of the flame retardants (flame retardants H to J) shown in FIG. 10 among the constituent materials constituting the composite material, and on the blending ratio shown in FIG. 10.

(2) Amount of Maleic Anhydride Denaturation

An amount of maleic anhydride denaturation is a parameter indicating the amount of maleic anhydride (MAH) contained in the composite material. Since maleic anhydride has a function of bonding the resin and the filler, the amount of maleic anhydride is considered to affect the elongation or the tensile strength of the resin composition, and thus is used as a parameter. For example, the synthesized characteristic value regarding the amount of maleic anhydride denaturation is related to the resin. Thus, the operation for calculating the synthesized characteristic value is performed based on the characteristic value of each of the resins (resins A to G) shown in FIG. 10 among the constituent materials constituting the composite material and on the blending ratio shown in FIG. 10.

(3) Amount of Crystals

An amount of crystals is a parameter indicating the amount of crystalline resin contained in the composite material. Since hardness of the composite material changes with the amount of crystalline resin, the amount of crystalline resin is considered to affect the elongation or the tensile strength of the resin composition, and thus is used as a parameter. For example, the synthesized characteristic value regarding the amount of crystals is related to the resin. Thus, the operation for calculating the synthesized characteristic value is performed based on the characteristic value of each of the resins (resins A to G) shown in FIG. 10 among the constituent materials constituting the composite material and on the blending ratio shown in FIG. 10.

(4) Amount of Vinyl Acetate Group

An amount of vinyl acetate groups is a parameter indicating the amount of the vinyl acetate groups contained in the composite material. Since hardness of the composite material changes with the amount of vinyl acetate groups, the amount of vinyl acetate groups is considered to affect the elongation or the tensile strength of the resin composition, and thus is used as a parameter. For example, the synthesized characteristic value regarding the amount of the vinyl acetate groups is related to the resin. Thus, the operation for calculating the synthesized characteristic value is performed based on the characteristic value of each of the resins (resins A to G) shown in FIG. 10 among the constituent materials constituting the composite material and on the blending ratio shown in FIG. 10.

(5) Filler Surface Area

A filler surface area is used as a parameter indicating the size of filler particles used as a flame retardant or a flame-retardant aid. The size of the filler particles is considered to affect the elongation or the tensile strength of the resin composition, and thus is used as a parameter. For example, the synthesized characteristic value regarding the filler surface area is related to the flame retardant. Thus, the operation for calculating the synthesized characteristic value is performed based on the characteristic value of each of the flame retardants (flame retardants H to J) shown in FIG. 10 among the constituent materials constituting the composite material and on the blending ratio shown in FIG. 10.

Next, the supplementary data included in the data shown in FIG. 11 will be described.

The supplementary data includes the categorical variable. The value of this categorical variable is input based on the blending data included in the data shown in FIG. 10.

The categorical variable is a digital variable, and the supplementary data uses, for example, four types of categorical variables. Specifically, the categorical variable "CAT1" indicates the type of surface treatment of the flame retardant. The variable value "1" indicates that the surface treatment of the flame retardant is a silane coupling treatment, whereas the variable value "0" indicates that no silane coupling treatment has been applied.

The categorical variable "CAT2" indicates the type of surface treatment of the flame retardant. The variable value "1" indicates that the surface treatment of the flame retardant is a fatty acid treatment, whereas the variable value "0" indicates that no fatty acid treatment has been applied.

The categorical variable "CAT3" indicates a component of the flame retardant. The variable value "1" indicates that the component of the flame retardant contains magnesium hydroxide, whereas the variable value "0" indicates that the component of the flame retardant does not contain magnesium hydroxide.

The categorical variable "CAT4" indicates a component of the flame retardant. The variable value "1" indicates that the component of the flame retardant contains aluminum hydroxide, whereas the variable value "0" indicates that the component of the flame retardant does not contain aluminum hydroxide.

For example, in FIG. 11, the composite material identified by the blending number "ID1" has the categorical variable "CAT1" of "1", the categorical variable "CAT2" of "0", the categorical variable "CAT3" of "1", and the categorical variable "CAT4" of "0". Thus, in the composite material identified by the blending number "ID1", it can be seen that the component of the flame retardant which is a constituent material contains magnesium hydroxide, and that the silane coupling treatment is applied as the surface treatment of the flame retardant.

Further, the additional data included in the data shown in FIG. 11 will be described.

The additional data includes the irradiation dose as the process condition value. This irradiation dose refers to the radiation dose of the radiation applied in a step of cross-linking the resin contained in the composite material. For example, the irradiation dose "0" means that the step of cross-linking the resin by applying radiation was not performed in the first place.

The data shown in FIG. 11 is configured in such a manner.

Next, the approximate function is generated based on the blending data shown in FIG. 10 and the data shown in FIG. 11 (synthesis-related data, supplementary data, and additional data). Specifically, the approximate function is generated by performing machine learning in which the blending data shown in FIG. 10 and the data shown in FIG. 11 are used for the teacher data, the inputs are the blending information, the synthesized characteristic value, the value of the categorical variable, and the value of the irradiation dose, and the output is the value of physical quantity. Thus, in the specific example, the approximate function is generated using the data shown in FIG. 11 as well as the blending information (blending data shown in FIG. 10) including the material names and the blending ratio as the teacher data. In this case, the approximate function in which the inputs are the blending information, the synthesized characteristic value, the value of the categorical variable, and the value of the irradiation dose, and the output is the value of physical quantity is generated.

Note that the approximate function may be generated by performing machine learning using not only all of the blending information, the synthesized characteristic value, the value of the categorical variable, and the value of the irradiation dose as the inputs, but also the blending information, the synthesized characteristic value, and the value of the categorical variable as the inputs and also the value of physical quantity as the output. In this case, the approximate function in which the inputs are the blending information, the synthesized characteristic value, and the variable value of the categorical variable, and the output is the value of physical quantity is generated. In addition, the approximate function in which the blending information, the synthesized characteristic value, and the process condition value (value of the irradiation dose) are the inputs and the value of physical quantity is the output may be generated by performing machine learning. In this case, the approximate function in which the inputs are the blending information, the synthesized characteristic value, and the process condition value, and the output is the value of physical quantity is generated.

Further, the approximate function in which the blending information and the synthesized characteristic value are the inputs and the value of physical quantity is the output may be generated by performing machine learning. In this case, the approximate function in which the inputs are the blending information and the synthesized characteristic value and the output is the value of physical quantity is generated.

Next, estimating the value of physical quantity for the first composite material of the evaluation target based on the approximate function generated in the above-described manner will be described.

FIG. 12 is a table showing the first blending data of the first composite material which becomes the evaluation target whose correspondence to the value of physical quantity is unknown. In FIG. 12, the blending number is the ID number for identifying the first composite material. Further, in FIG. 12, the constituent materials constituting the first composite material include resins, a flame retardant (filler), antioxidants, lubricants, a coloring agent, and a cross-linking aid.

The resins are indicated by the material names of resin A, resin D, resin F, and resin G. In addition, the flame retardant is indicated by the material name of flame retardant I. Further, the antioxidants are indicated by the material names of antioxidant K and antioxidant L, and the lubricants are indicated by the material names of lubricant M and lubricant O. In addition, the coloring agent is indicated by the material name of coloring agent P, and the cross-linking aid is indicated by the material name of cross-linking aid Q.

In FIG. 12, for example, the first composite material identified by the blending number "ID100" contains, as constituent materials, the resin A (45 parts by mass), the resin D (40 parts by mass), the resin F (15 parts by mass), the flame retardant I (160 parts by mass), the antioxidant K (1 part by mass), the antioxidant L (2 parts by mass), the lubricant M (1 part by mass), the lubricant O (2 parts by mass), the coloring agent P (2 parts by mass), and the cross-linking aid Q (4 parts by mass). Thus, it can be seen that the data shown in FIG. 12 is the first blending data (blending information) including the material names and the blending ratio of the constituent materials constituting the first composite material.

Next, in the specific example, data shown in FIG. 13 is generated based on the first blending data shown in FIG. 12. The data shown in FIG. 13 is constituted by the first synthesized characteristic value, a value of a first categorical variable and a value of a first irradiation dose.

In the specific example, the first synthesized characteristic value of the first composite material is calculated based on the first blending data shown in FIG. 12 and the first characteristic value data (not shown). Specifically, the first synthesized characteristic value of the first composite material is calculated based on the first blending ratio of the constituent materials contained in the first composite material and the characteristic value corresponding to the constituent materials contained in the first composite material. For example, the first synthesized characteristic value is calculated by performing the operation of synthesizing the characteristic values of the first characteristic value data based on the first blending ratio of the first blending data shown in FIG. 12 and on the first characteristic value data (not shown) corresponding to the constituent materials contained in the first composite material. Note that the first characteristic value data refers to data in which the material name of the constituent material contained in the first composite material and the characteristic value of the constituent material are associated with each other, and is data obtained in advance. For example, when focusing on the resin D shown in FIG. 12, the first characteristic value data refers to data in which the material name "resin D" and the characteristic value of the resin D are associated with each other.

In addition, the value of the first categorical variable is input based on the first blending data shown in FIG. 12. Likewise, the value of the first irradiation dose is also input based on the first blending data shown in FIG. 12. Here, the value of the first categorical variable refers to the value of the categorical variable for the first composite material, and the value of the first irradiation dose refers to the value of the irradiation dose for the first composite material.

For example, the first composite material identified by the blending number "ID100" has the filler volume ratio of "0.6", the amount of maleic anhydride denaturation of "0.3", the amount of crystals of "27", the amount of vinyl acetate group of "32", and the filler surface area of "643". In addition, the first composite material identified by the blending number "ID100" has the first categorical variables "CAT1" of "1", "CAT2" of "0", "CAT3" of "0", and "CAT4" of "1", and the first irradiation dose of "0".

Next, the material names and the first blending ratio included in the first blending data shown in FIG. 12, and the first synthesized characteristic value, the value of the first categorical variable, and the value of the first irradiation dose shown in FIG. 13 are input to the approximate function to estimate the value of physical quantity for the first composite material. As a result, as shown in the table of FIG. 14, the estimated value of physical quantity is output. For example, in FIG. 14, it can be seen that a value of "13.15" for the tensile strength (physical quantity) is output for the first composite material identified by the blending number "ID100".

In this manner, the specific example makes it possible to output the value of physical quantity that is highly likely to be realized for the first composite material which becomes the evaluation target whose correspondence to the value of physical quantity is unknown.

In particular, the specific example uses not only the first synthesized characteristic value but also the blending information including the material names and the blending ratio of the constituent materials as the input parameters for the approximate function. For this reason, according to the specific example, it is possible to improve estimation accuracy of the value of physical quantity by providing more types of input parameters for the approximate function. Note that, in the specific example, as an example of the input parameter for the approximate function using the first synthesized characteristic value and the blending information including the material names and the blending ratio of the constituent materials, the first categorical variable and the first irradiation dose are also used as the input parameters for the approximate function.

However, in the applied concept, the first categorical variable and the first irradiation dose (process condition value) are not required input parameters, and it is possible to estimate the value of physical quantity that is more accurate than in the basic concept if at least the first synthesized characteristic value and the blending information including the material names and the blending ratio of the constituent materials are included in the input parameters for the approximate function.

<Verification of Effects>

Hereinafter, results in verifying that the value of physical quantity can be estimated with high accuracy according to the applied concept in which the value of physical quantity is estimated by the approximate function using the synthesized characteristic value and the blending information including the material names and the blending ratio as the input parameters will be described.

(1) Methods of Examination
  (A) Use the blending information (material name) as the input parameter
  (B) Use the synthesized characteristic value as the input parameter
  (C) Use both the blending information and the synthesized characteristic value as the input parameters Here, the synthesized characteristic values include a filler volume fraction, the amount of crystals, an amount of copolymerization, the amount of maleic anhydride denaturation, and a BET specific surface area.

Five non-linear methods listed below were used as regression methods.
(a) Support vector regression (SVR)
(b) Gaussian process regression (GPR)
(c) Light GBM (LGBM)
(d) Random forest (RF)
(e) Neural network (NN)

To build a model, a total blending data was randomly divided into training data and test data at a ratio of 7:3. The model was trained using the training data, and was evaluated using the test data. The average of 30 evaluations was used as an evaluation value. The evaluation was performed using a mean absolute percentage error (MAPE), a mean absolute error (MAE), and an "$R^2$ value".

(2) Verification Results (2-1) Initial Tensile Strength and Initial Elongation

Figure 15:
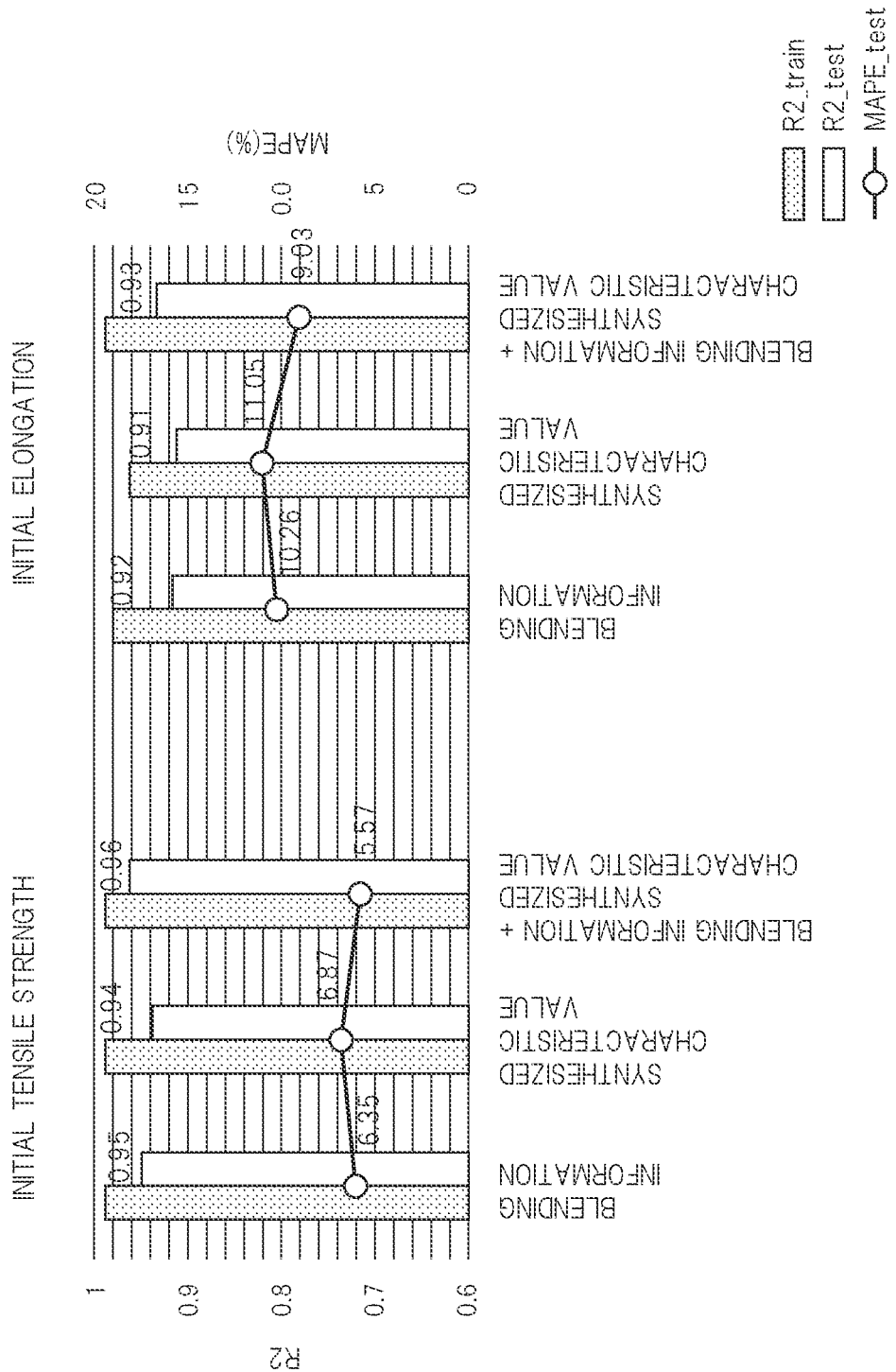
FIG. 15 is a graph showing verification results regarding initial tensile strength and initial elongation.

FIG. 15 is a graph showing verification results regarding initial tensile strength and initial elongation. As shown in FIG. 15, when the input parameter was changed from "blending information" to "blending information+synthesized characteristic value", MAPE changed from 6.3% to 5.6% for the initial tensile strength, and changed from 10.3% to 9.0% for the initial elongation. In addition, the $R^2$ value which is a determination coefficient increased. Considering that a smaller value for MAPE means a more accurate prediction and that an increase in the $R^2$ value means a more accurate prediction, it can be seen that changing the input parameter from "blending information" to "blending information+synthesized characteristic value" improves the prediction accuracy of the initial tensile strength and the initial elongation.

(2-2) Residual Aging Rate (for Tensile Strength)

Figure 16:
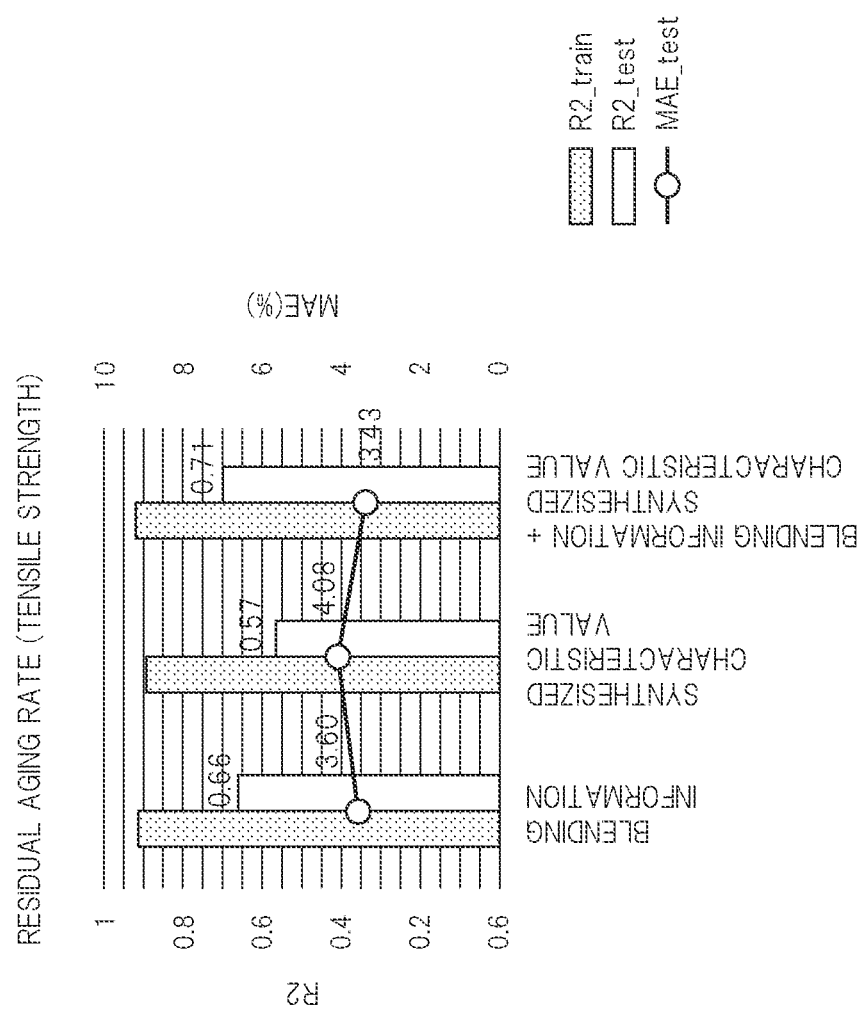
FIG. 16 is a graph showing verification results regarding a residual aging rate of the tensile strength.

FIG. 16 is a graph showing verification results of a residual aging rate of the tensile strength. As shown in FIG. 16, when the input parameter was changed from "blending information" to "blending information+synthesized characteristic value", MAE changed from 3.6% to 3.4% for the residual aging rate of the tensile strength, and the $R^2$ value increased from "0.66" to "0.71". Therefore, it can be seen that changing the input parameter from "blending information" to "blending information+synthesized characteristic value" improves the prediction accuracy of the residual aging rate of the tensile strength.

(2-3) Residual Oil Resistance (of Tensile Strength) and Residual Oil Resistance (of Elongation)

Figure 17:
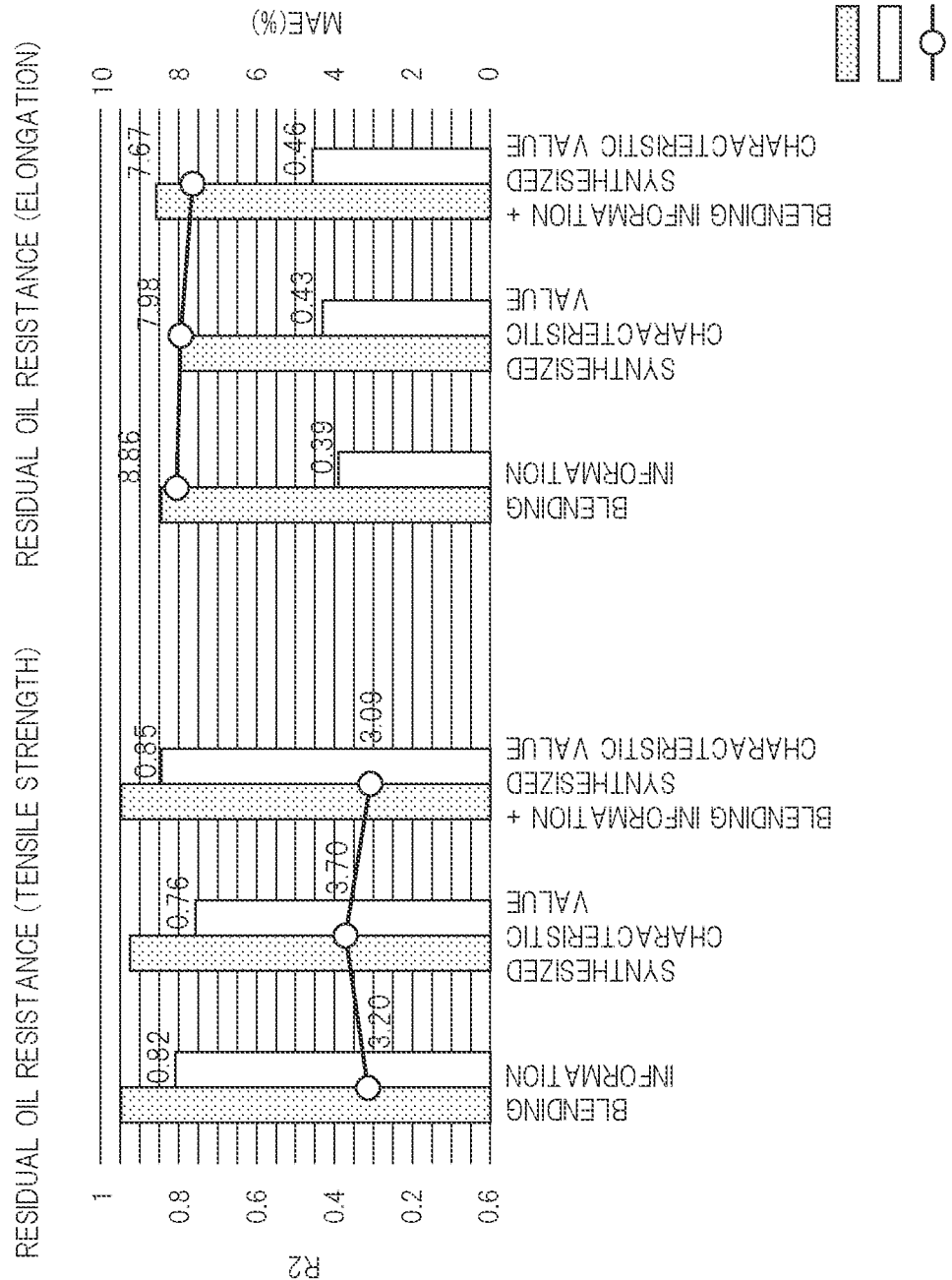
FIG. 17 is a graph showing verification results regarding residual oil resistance of the tensile strength and residual oil resistance of the elongation.

FIG. 17 is a graph showing verification results regarding residual oil resistance of the tensile strength and residual oil resistance of the elongation. As shown in FIG. 17, when the input parameter was changed from "blending information" to "blending information+synthesized characteristic value", MAE changed from 3.2% to 3.1% for the residual oil resistance of the tensile strength, and the $R^2$ value increased from "0.82" to "0.85". In addition, when the input parameter was changed from "blending information" to "blending information+synthesized characteristic value", MAE changed from 8.1% to 7.7% for the residual oil resistance of the elongation, and the $R^2$ value increased from "0.39" to "0.46". Therefore, it can be seen that changing the input parameter from "blending information" to "blending information+synthesized characteristic value" improves the prediction accuracy of both the residual oil resistance of the tensile strength and the residual oil resistance of the elongation.

(2-4) Residual Fuel Resistance (Tensile Strength) and Residual Fuel Resistance (Elongation)

Figure 18:
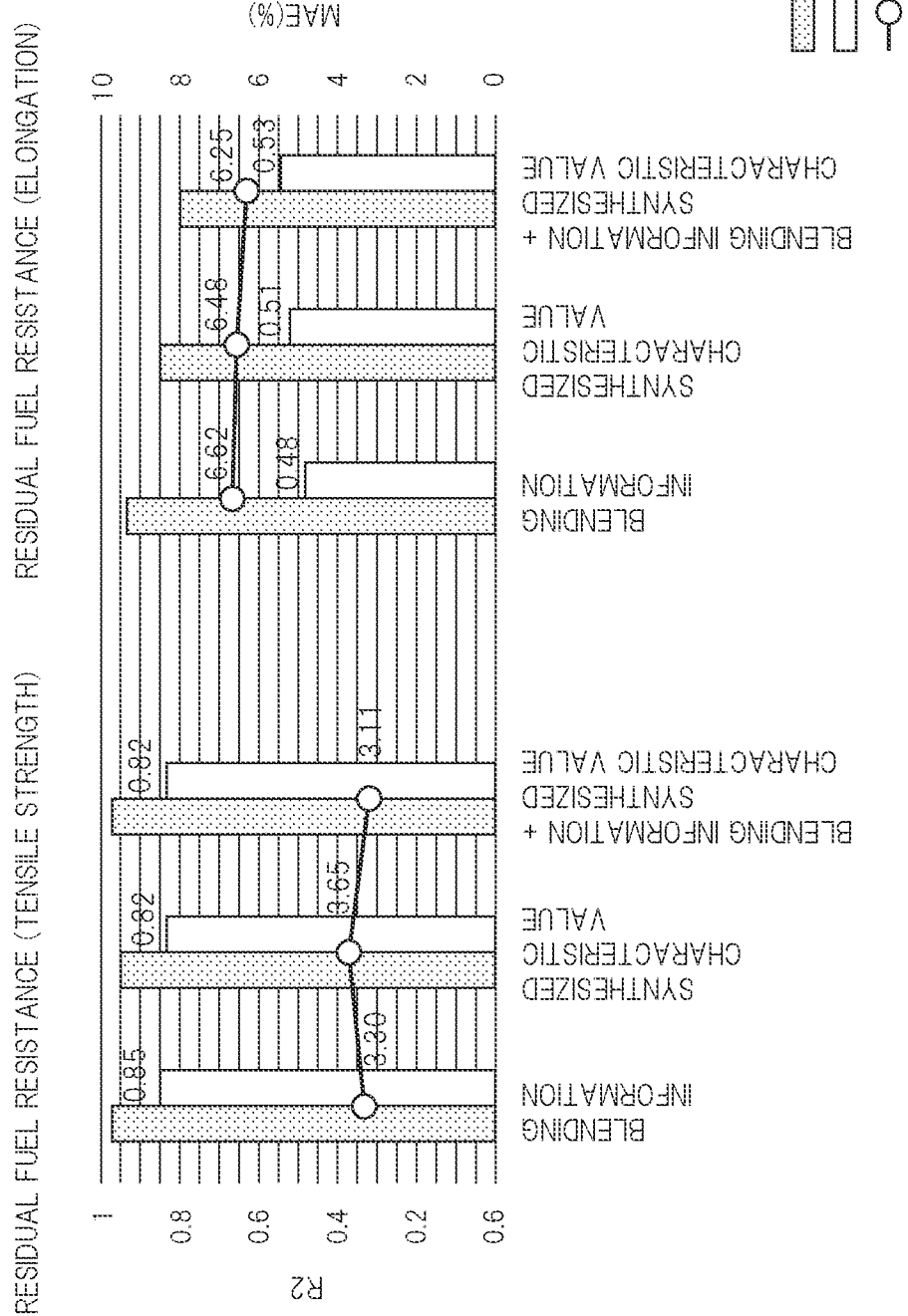
FIG. 18 is a graph showing verification results regarding residual fuel resistance of the tensile strength and residual fuel resistance of the elongation.

FIG. 18 is a graph showing verification results regarding residual fuel resistance of the tensile strength and residual fuel resistance of the elongation. As shown in FIG. 18, when the input parameter was changed from "blending information" to "blending information+synthesized characteristic value", MAE changed from 3.3% to 3.1% for the residual fuel resistance of the tensile strength. In addition, when the input parameter was changed from "blending information" to "blending information+synthesized characteristic value", MAE changed from 6.6% to 6.3% for the residual fuel resistance of the elongation, and the $R^2$ value increased from "0.48" to "0.53". Therefore, it can be seen that changing the input parameter from "blending information" to "blending information+synthesized characteristic value" improves the prediction accuracy of both the residual fuel resistance of the tensile strength and the residual fuel resistance of the elongation.

(2-5) Low-Temperature Elongation

Figure 19:
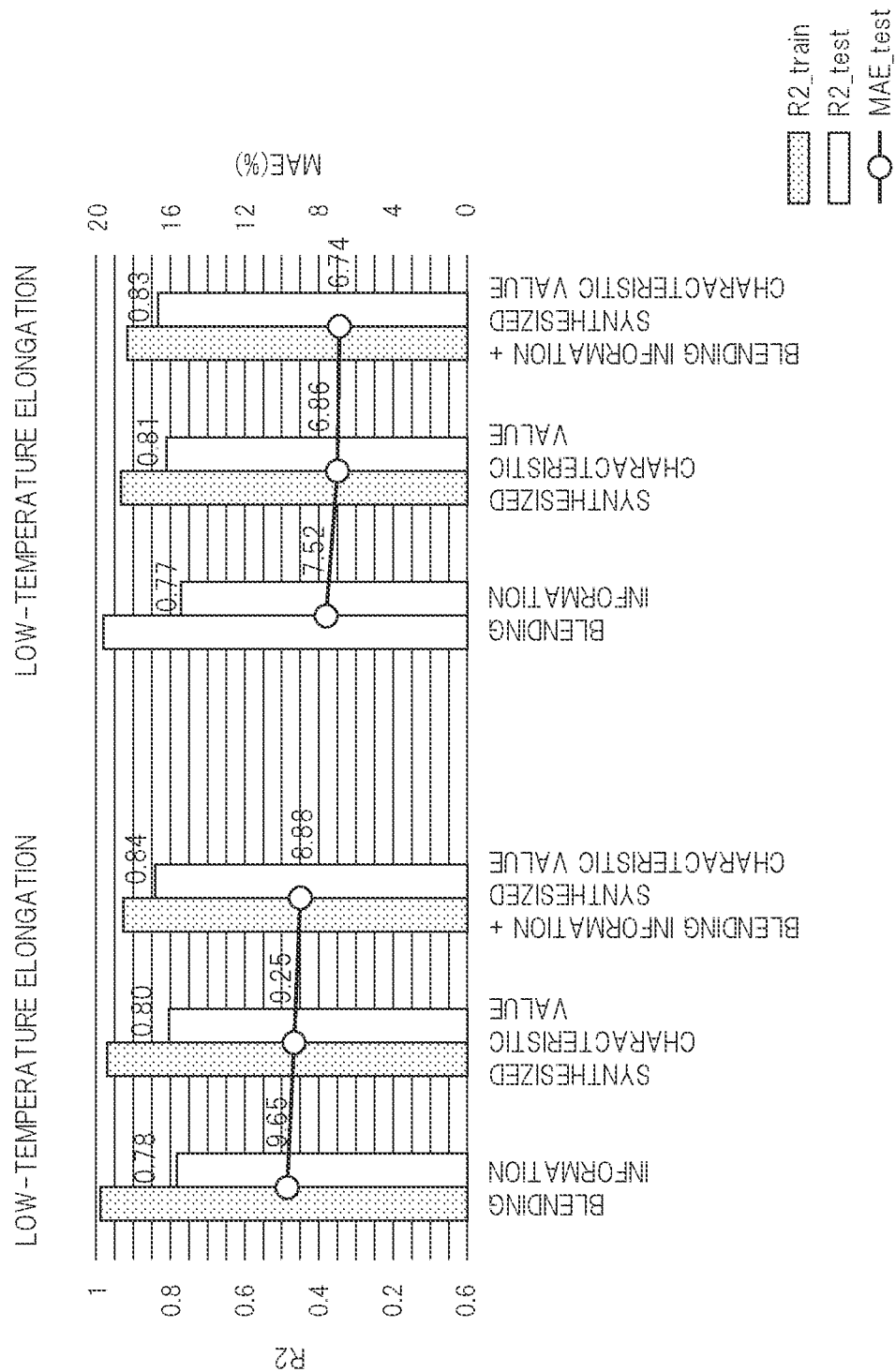
FIG. 19 is a graph showing verification results regarding low-temperature elongation.

FIG. 19 is a graph showing verification results regarding elongation at −40° C. and elongation at −50° C. As shown in FIG. 19, when the input parameter was changed from "blending information" to "blending information+synthesized characteristic value", MAE changed from 9.7% to 8.9% for the elongation at −40° C., and the $R^2$ value increased from "0.78" to "0.84". In addition, when the input parameter was changed from "blending information" to "blending information+synthesized characteristic value", MAE changed from 7.5% to 6.7% for the elongation at −50° C., and the $R^2$ value increased from "0.77" to "0.83". Therefore, it can be seen that changing the input parameter from "blending information" to "blending information+synthesized characteristic value" improves the prediction accuracy of both the elongation at −40° C. and the elongation at −50° C.

From the above, it can be seen that the accuracy for estimating the values of various physical quantities can be improved by changing the input parameter from "blending information" to "blending information+synthesized characteristic value". Namely, the above-described verification results support the fact that the applied concept can be used to improve estimation accuracy of the value of physical quantity compared to that of the basic concept.

In the foregoing, the invention made by the present inventors has been specifically described based on the embodiments. However, it goes without saying that the present invention is not limited to these embodiments, and various modifications can be made without departing from the scope of the invention.

What is claimed is:

1. A physical quantity estimating system configured to estimate a value of physical quantity for a composite material containing two or more materials belonging to a plurality of different materials as constituent materials, the physical quantity estimating system comprising:

an approximate function generating unit configured to generate, when a first synthesized characteristic value of a first composite material whose value of physical quantity is unknown and first blending information including material names and a first blending ratio of the constituent materials contained in the first composite material are input, an approximate function for outputting the value of physical quantity for the first composite material;

a synthesized characteristic value calculating unit configured to calculate the first synthesized characteristic value of the first composite material based on the first blending ratio of the constituent materials contained in the first composite material and on first characteristic values corresponding to the constituent materials contained in the first composite material; and a physical quantity estimating unit configured to estimate the value of physical quantity for the first composite material based on the first synthesized characteristic value, the first blending information, and the approximate function.

2. The physical quantity estimating system according to claim 1, wherein the approximate function generating unit is configured to generate, when the first synthesized characteristic value, the first blending information, and a variable value of a first categorical variable which is a digital variable are input, the approximate function for outputting the value of physical quantity for the first composite material, and wherein the physical quantity estimating unit is configured to estimate the value of physical quantity for the first composite material based on the first synthesized characteristic value, the first blending information, the variable value of the first categorical variable, and the approximate function.

3. The physical quantity estimating system according to claim 1, wherein the approximate function generating unit is configured to generate, when the first synthesized characteristic value, the first blending information, and a first process condition value are input, the approximate function for outputting the value of physical quantity for the first composite material, and wherein the physical quantity estimating unit is configured to estimate the value of physical quantity for the first composite material based on the first synthesized characteristic value, the first blending information, the first process condition value, and the approximate function.

4. The physical quantity estimating system according to claim 3, wherein the first process condition value includes a value of a radiation dose in a cross-linking process of resin.

5. The physical quantity estimating system according to claim 1, wherein the physical quantity includes elongation or tensile strength.

6. An approximate function generating apparatus that is a component of a physical quantity estimating system configured to estimate a value of physical quantity for a composite material containing two or more materials belonging to a plurality of different materials as constituent materials, wherein the approximate function generating apparatus comprises an approximate function generating unit configured to generate, when a first synthesized characteristic value of a first composite material whose value of physical quantity is unknown and first blending information including material names and a first blending ratio of the constituent materials contained in the first composite material are input, an approximate function for outputting the value of physical quantity for the first composite material, and a synthesized characteristic value calculating unit configured to calculate the first synthesized characteristic value of the first composite material based on the first blending ratio of the constituent materials contained in the first composite material and on first characteristic values corresponding to the constituent materials contained in the first composite material.

7. The approximate function generating apparatus according to claim 6, wherein the approximate function generating unit is configured to generate, when the first synthesized characteristic value, the first blending information, and a variable value of a first categorical variable which is a digital variable are input, the approximate function for outputting the value of physical quantity for the first composite material.

8. The approximate function generating apparatus according to claim 6, wherein the approximate function generating unit is configured to generate, when the first synthesized characteristic value, the first blending information, and a first process condition value are input, the approximate function for outputting the value of physical quantity for the first composite material.

9. A physical quantity estimating apparatus that is a component of a physical quantity estimating system configured to estimate a value of physical quantity for a composite material containing two or more materials belonging to a plurality of different materials as constituent materials, the physical quantity estimating apparatus comprising:

a synthesized characteristic value calculating unit configured to calculate, based on a first blending ratio of the constituent materials contained in a first composite material whose value of physical quantity is unknown and on first characteristic values corresponding to the constituent materials contained in the first composite material, a first synthesized characteristic value of the first composite material; and a physical quantity estimating unit configured to estimate the value of physical quantity for the first composite material based on the first synthesized characteristic value, first blending information including material names and the first blending ratio of the constituent materials contained in the first composite material, and an approximate function, wherein the approximate function is a function for outputting the value of physical quantity for the first composite material when the first synthesized characteristic value and the first blending information are input.

10. The physical quantity estimating apparatus according to claim 9, wherein the approximate function is a function for outputting the value of physical quantity for the first composite material when the first synthesized characteristic value, the first blending information, and a variable value of a first categorical variable which is a digital variable are input, and wherein the physical quantity estimating unit is configured to estimate the value of physical quantity for the first composite material based on the first synthesized characteristic value, the first blending information, the variable value of the first categorical variable, and the approximate function.

11. The physical quantity estimating apparatus according to claim 9, wherein the approximate function is a function for outputting the value of physical quantity for the first composite material when the first synthesized characteristic value, the first blending information, and a first process condition value are input, and wherein the physical quantity estimating unit is configured to estimate the value of physical quantity for the first composite material based on the first synthesized characteristic value, the first blending information, the first process condition value, and the approximate function.

12. A physical quantity estimating method in which a computer estimates a value of physical quantity for a composite material containing two or more materials belonging to a plurality of different materials as constituent materials, the physical quantity estimating method including:
   an approximate function generating step in which an approximate function generating unit of the computer generates, when a first synthesized characteristic value of a first composite material whose value of physical quantity is unknown and first blending information including material names and a first blending ratio of the constituent materials contained in the first composite material are input, an approximate function for outputting the value of physical quantity for the first composite material;
   a synthesized characteristic value calculating step in which a synthesized characteristic value calculating unit of the computer calculates the first synthesized characteristic value of the first composite material based on the first blending ratio of the constituent materials contained in the first composite material and on first characteristic values corresponding to the constituent materials contained in the first composite material; and
   a physical quantity estimating step in which a physical quantity estimating unit of the computer estimates the value of physical quantity for the first composite material based on the first synthesized characteristic value, the first blending information, and the approximate function.

13. The physical quantity estimating method according to claim 12,
   wherein, in the approximate function generating step, the approximate function generating unit of the computer generates, when the first synthesized characteristic value, the first blending information, and a variable value of a first categorical variable which is a digital variable are input, the approximate function for outputting the value of physical quantity for the first composite material, and
   wherein, in the physical quantity estimating step, the physical quantity estimating unit of the computer estimates the value of physical quantity for the first composite material based on the first synthesized characteristic value, the first blending information, the variable value of the first categorical variable, and the approximate function.

14. The physical quantity estimating method according to claim 12,
   wherein, in the approximate function generating step, the approximate function generating unit of the computer generates, when the first synthesized characteristic value, the first blending information, and a first process condition value are input, the approximate function for outputting the value of physical quantity for the first composite material, and
   wherein, in the physical quantity estimating step, the physical quantity estimating unit of the computer estimates the value of physical quantity for the first composite material based on the first synthesized characteristic value, the first blending information, the first process condition value, and the approximate function.

* * * * *